US010012641B2

(12) United States Patent
Rathbone et al.

(10) Patent No.: US 10,012,641 B2
(45) Date of Patent: Jul. 3, 2018

(54) G-PROTEIN-COUPLED-RECEPTOR-22-TRANSFORMED CELL LINES AND METHODS OF USE THEREOF TO IDENTIFY BINDING COMPOUNDS

(71) Applicant: LIBRAMEN NATURALS INC., Ontario (CA)

(72) Inventors: Michel P. Rathbone, Ontario (CA); Shucui Jiang, Ontario (CA); Francesco Caciagli, Chieti (IT); Renata Ciccarelli, Chieti (IT); Patrizia Ballerini, Chieti (IT); Patrizia Di Iorio, Chieti (IT); Patricia Giuliani, Chieti (IT); Iolanda D'Alimonte, Chieti (IT)

(73) Assignee: LIBRAMEN NATURALS INC., Ontario (CA)

( * ) Notice: Subject to any disclaimer, the term of this patent is extended or adjusted under 35 U.S.C. 154(b) by 0 days.

(21) Appl. No.: 15/331,372

(22) Filed: Oct. 21, 2016

(65) Prior Publication Data
US 2017/0115277 A1 Apr. 27, 2017

Related U.S. Application Data

(63) Continuation of application No. PCT/CA2015/050326, filed on Apr. 20, 2015.

(60) Provisional application No. 61/984,618, filed on Apr. 25, 2014, provisional application No. 61/985,373, filed on Apr. 28, 2014.

(51) Int. Cl.
*G01N 33/50* (2006.01)
*C07K 14/705* (2006.01)
*C12N 5/00* (2006.01)

(52) U.S. Cl.
CPC ....... *G01N 33/5041* (2013.01); *C07K 14/705* (2013.01); *C12N 5/00* (2013.01); *C12N 2510/00* (2013.01); *G01N 2333/705* (2013.01)

(58) Field of Classification Search
CPC ......... G01N 33/5041; G01N 2333/705; C07K 14/705; C12N 5/00; C12N 2510/00
See application file for complete search history.

(56) References Cited

U.S. PATENT DOCUMENTS 7,611,832 B2 * 11/2009 Adams ............... C07K 14/705
435/4
2009/0010909 A1  1/2009  Ruiz-Lozano
2011/0214189 A1  9/2011  Gaitanaris et al.

FOREIGN PATENT DOCUMENTS

WO  2000022129 A9  9/2000
WO   200183550 A2  11/2001
WO  2005047905 A1  5/2005
WO  2007047520 A1  4/2007
WO  2008061209 A2  5/2008

OTHER PUBLICATIONS

ERB et al. "Site-directed Mutagenesis of P2U Purinoreceptors." The Journal of Biological Chemistry, Mar. 3, 1995, vol. 270(9), p. 4185-4188.
International Search Report (Corrected Version) for PCT/2015/050326, dated Jun. 22, 2015. 3 pages.
International Search Report for PCT/2015/050326, dated Jun. 22, 2015. 7 pages.
Milligen, G "Strategies to Identify Ligands for Orphan G-Protein-Couple Receptors" Biochemical Society Transactions, 2002, vol. 30(4), pp. 789-793.
Van Poyer, et al. "Phenolamine-dependent Adenylyl Cyclase Acitivation in Drosphilia Schneider 2 Cells." Insect Biochemistry and Molecular Biology, 2001, 31, pp. 333-338.
Written Opinion for PCT/2015/050326, dated Jun. 9, 2015. 5 pages.
Adams, J.W., et al: "Myocardial expression, signalling, and function of GPR22: a protective role for an orphan G protein-coupled receptor", American Journal of Physiology: Heart and Circulatory Physiology, vol. 295, No. 2, Jun. 6, 2008 (Jun. 6, 2008), pp. H509-H521, US ISSN: 0363-6135, DOI: 10.1152/ajpheart.00368. 2008.
European Supplementary Search Report for EP3134433, dated Sep. 1, 2017.
Jiang, S. et al: "How does extracellular guanosine regulate some of its biological effects?", Purinergic Signalling, Springer Verlag, DE, vol. 10, No. 4, Dec. 1, 2014 (Dec. 1, 2014), p. 736,, ISSN: 1573-9538.
Milligan, G., "High-Throughput Screening: The Way Ahead Strategies to identify ligands for orphan G-protein-coupled receptors", Biochemical Society Transactions, vol. 30, No. 4, Jan. 1, 2002 (Jan. 1, 2002), pp. 789-793.
Su C, Picard P., et al. "Guanosine-induced decrease in side population of lung cancer cells: lack of correlation with ABCG2 expression". J Biol Regul Homeost Agents, vol. 24, No. 1, 2010, pp. 19-25.
Su C, Wang P., et al. "Guanosine promotes proliferation of neural stem cells through cAMP-CREB pathway". J Biol Regul Homeost Agents. vol. 27, No. 3, 2013, pp. 673-680 (Abstract).
Su, Caixin, et al. "Guanosine Improves Motor Behavior, Reduces Apoptosis, and Stimulates Neurogenesis in Rats with Parkinsonism." Journal of Neuroscience Research, vol. 87, No. 3, 2009, pp. 617-625., doi:10.1002/jnr.21883.

(Continued)

*Primary Examiner* — Robert S Landsman
(74) *Attorney, Agent, or Firm* — Stein IP, LLC

(57) ABSTRACT

Disclosed herein are cell lines transformed to express G-Protein Coupled Receptor GPCR22 and uses thereof for identifying guanosine analogs and/or other ligands to the receptor. In particular, techniques for transforming *Drosophila* Schneider 2 cells and human astrocytoma 1321N1 cell to express GPCR22 are disclosed as well as transformed cells lines. The transformed cell lines of the instant disclosure may be useful in identifying guanosine analogs and functional equivalents thereof.

13 Claims, 25 Drawing Sheets

(56) References Cited

OTHER PUBLICATIONS

Tavares, Rejane G., et al. "In Vivo Quinolinic Acid Increases Synaptosomal Glutamate Release in Rats: Reversal by Guanosine." Neurochemical Research, vol. 30, No. 4, 2005, pp. 439-444., doi:10.1007/s11064-005-2678-0.

Thauerer, Bettina, et al. "Vital Role of Protein Kinase C-Related Kinase in the Formation and Stability of Neurites during Hypoxia." Journal of Neurochemistry, vol. 113, No. 2, 2010, pp. 432-446., doi:10.1111/j.1471-4159.2010.06624.x.

Thomazi, Ana Paula, et al. "Profile of Glutamate Uptake and Cellular Viability in Hippocampal Slices Exposed to Oxygen and Glucose Deprivation: Developmental Aspects and Protection by Guanosine." Brain Research, vol. 1188, 2008, pp. 233-240., doi:10.1016/j.brainres.2007.10.037.

Traversa, Ugo, et al. "Rat Brain Guanosine Binding Site: Biological Studies and Pseudo-Receptor Construction." Bioorganic and Medicinal Chemistry, vol. 11, No. 24, 2003, pp. 5417-5425., doi:10.1016/j.bmc.2003.09.043.

Traversa, Ugo, et al. "Specific [3H]-Guanosine Binding Sites in Rat Brain Membranes." British Journal of Pharmacology, vol. 135, No. 4, 2002, pp. 969-976., doi:10.1038/sj.bjp.0704542.

Volpini, Rosaria, et al. "Evidence for the Existence of a Specific G Protein-Coupled Receptor Activated by Guanosine." ChemMedChem, vol. 6, No. 6, 2011, pp. 1074-1080., doi:10.1002/cmdc.201100100.

Wengert, M., et al. "Adenine-Induced Inhibition of Na -ATPase Activity: Evidence for Involvement of the Gi Protein-Coupled Receptor in the CAMP Signaling Pathway." Archives of Biochemistry and Biophysics, vol. 467, No. 2, 2007, pp. 261-267., doi:10.1016/j.abb.2007.08.018.

Wu, W.-P, et al. "Decreased Inflammatory Pain Due to Reduced Carrageenan-Induced Inflammation in Mice Lacking Adenosine A3 Receptors." Neuroscience, vol. 114, No. 3, 2002, pp. 523-527., doi:10.1016/s0306-4522(02)00273-7.

Ballerini, P., et al. "P2Y2 Receptor Up-Regulation Induced by Guanosine or UTP in Rat Brain Cultured Astrocytes." International Journal of Immunopathology and Pharmacology, vol. 19, No. 2, 2006, pp. 293-308., doi:10.1177/039463200601900207.

Ballerini, Patrizia, et al. "Guanosine Effect on Cholesterol Efflux and Apolipoprotein E Expression in Astrocytes." Purinergic Signalling, vol. 2, No. 4, 2006, pp. 637-649. doi:10.1007/s11302-006-9011-5.

Bau, Christian, et al. "Guanosine Stimulates Neurite Outgrowth in PC12 Cells via Activation of Heme Oxygenase and Cyclic GMP." Purinergic Signalling, vol. 1, No. 2, Jul. 2005, pp. 161-172., doi:10.1007/s11302-005-6214-0.

Benfenati, Valentina, et al. "Guanosine Promotes the up-Regulation of Inward Rectifier Potassium Current Mediated by Kir4.1 in Cultured Rat Cortical Astrocytes." Journal of Neurochemistry, vol. 98, No. 2, 2006, pp. 430-445., doi:10.1111/i.1471-4159.2006.03877.x.

Borea, Pier Andrea, et al. "Full and Partial Agonistic Behaviour and Thermodynamic Binding Parameters of Adenosine A1 Receptor Ligands." European Journal of Pharmacology: Molecular Pharmacology, vol. 267, No. 1, 1994, pp. 55-61., doi:10.1016/0922-4106(94)90224-0.

Burnstock, G. "Purine and Pyrimidine Receptors." Cellular and Molecular Life Sciences, vol. 64, No. 12, 2007, pp. 1471-1483., doi:10.1007/s00018-007-6497-0.

Chambers JK, Macdonald MM., et al. "A G protein-coupled receptor for UDP-glucose". Journal Biological Chemistry, vol. 275, No. 15, Apr. 2000, pp. 10767-10771.

Chang, Ruby, et al. "Neuroprotective Effects of Guanosine on Stroke Models in Vitro and in Vivo." Neuroscience Letters, vol. 431, No. 2, 2008, pp. 101-105., doi:10.1016/j.neulet.2007.11.072.

Chen, Ye, et al. "Guanosine-Induced Increase in Free Cytosolic Calcium Concentration in Mouse Astrocytes in Primary Cultures: Does It Act on an A3 Adenosine Receptor?" Journal of Neuroscience Research, vol. 65, No. 2, 2001, pp. 184-189., doi:10.1002/jnr.1141.

Ciccarelli, Renata, et al. "Cultured Astrocyte Proliferation Induced by Extracellular Guanosine Involves Endogenous Adenosine and Is Raised by the Co-Presence of Microglia." Glia, vol. 29, No. 3, Jan. 2000, pp. 202-211., doi:10.1002/(sici)1098-1136(20000201)29:3<202::aid-glia2>3.0.co;2-c.

Communi, Didier, et al. "Cotranscription and Intergenic Splicing of HumanP2Y11andSSF1Genes." Journal of Biological Chemistry, vol. 276, No. 19, May 2001, pp. 16561-16566., doi:10.1074/jbc.m009609200.

Connell, Barry J., et al. "Guanosine Protects against Reperfusion Injury in Rat Brains after Ischemic Stroke." Journal of Neuroscience Research, vol. 91, No. 2, 2013, pp. 262-272., doi:10.1002/jnr.23156.

Dionisotti, Silvio, et al. "Characterization of Human A2Aadenosine Receptors with the Antagonist Radioligand [3H]-SCH 58261." British Journal of Pharmacology, vol. 121, No. 3, 1997, pp. 353-360., doi:10.1038/sj.bjp.0701119.

Fields, Timothy A., and Patrick J. Casey. "Signalling Functions and Biochemical Properties of Pertussis Toxin-Resistant G-Proteins." Biochemical Journal, vol. 321, No. 3, Jan. 1997, pp. 561-571., doi:10.1042/bj3210561.

Fredholm BB, IJzerman AP, et al. "International Union of Pharmacology. XXV. Nomenclature and classification of adenosine receptors". vol. 53, No. 4, 2001, pp. 527-552.

Fumagalli, Marta, et al. "Nucleotide-Mediated Calcium Signaling in Rat Cortical Astrocytes: Role of P2X and P2Y Receptors." Glia, vol. 43, No. 3, 2003, pp. 218-230., doi:10.1002/glia.10248.

Gao, Z.-G. "Selective Allosteric Enhancement of Agonist Binding and Function at Human A3 Adenosine Receptors by a Series of Imidazoquinoline Derivatives." Molecular Pharmacology, vol. 62, No. 1, Jan. 2002, pp. 81-89., doi:10.1124/mol.62.1.81.

Giuliani P, Romano S., et al. "Protective activity of guanosine in an in vitro model of Parkinson's disease". Panminerva Med. vol. 54, No. 1 supp. 4, 2012, pp. 43-51.

Gomez, G. "Differential Requirement for A2a and A3 Adenosine Receptors for the Protective Effect of Inosine in Vivo." Blood, vol. 102, No. 13, 2003, pp. 4472-4478., doi:10.1182/blood-2002-11-3624.

Gysbers, John W., and Michel P. Rathbone. "Guanosine Enhances NGF-Stimulated Neurite Outgrowth in PC12 Cells." NeuroReport, vol. 3, No. 11, 1992, pp. 997-1000., doi:10.1097/00001756-199211000-00013.

Gysbers, John W., and Michel P. Rathbone. "Neurite Outgrowth in PC12 Cells Is Enhanced by Guanosine through Both CAMP-Dependent and -Independent Mechanisms." Neuroscience Letters, vol. 220, No. 3, 1996, pp. 175-178., doi:10.1016/s0304-3940(96)13253-5.

Haskó, György, et al. "Immunomodulatory and Neuroprotective Effects of Inosine." Trends in Pharmacological Sciences, vol. 25, No. 3, 2004, pp. 152-157., doi:10.1016/j.tips.2004.01.006.

Hindley, Shaun, et al. "Nitric Oxide Donors Enhance Neurotrophin-Induced Neurite Outgrowth through a CGMP-Dependent Mechanism." Journal of Neuroscience Research, vol. 47, No. 4, 1997, pp. 427-439., doi:10.1002/(sici)1097-4547(19970215)47:4<427::aid-jnr8>3.3.co;2-1.

Di Iorio, Patrizia, et al. "Mechanisms of Apoptosis Induced by Purine Nucleosides in Astrocytes." Glia, vol. 38, No. 3, Dec. 2002, pp. 179-190., doi:10.1002/glia.10055.

Jiang, Shucui, et al. "Enteric Glia Promote Regeneration of Transected Dorsal Root Axons into Spinal Cord of Adult Rats." Experimental Neurology, vol. 181, No. 1, 2003, pp. 79-83., doi:10.1016/s0014-4886(02)00030-4.

Jiang, Shucui, et al. "Guanosine Reduces Apoptosis and Inflammation Associated with Restoration of Function in Rats with Acute Spinal Cord Injury." Purinergic Signalling, vol. 3, No. 4, 2007, pp. 411-421., doi:10.1007/s11302-007-9079-6.

Jiang, Shucui, et al. "Non-Adenine Based Purines Accelerate Wound Healing." Purinergic Signalling, vol. 2, No. 4, 2006, pp. 651-661., doi:10.1007/s11302-006-9022-2.

Jiang, Shucui, et al. "Remyelination after Chronic Spinal Cord Injury Is Associated with Proliferation of Endogenous Adult Progenitor Cells after Systemic Administration of Guanosine." Purinergic Signalling, vol. 4, No. 1, Aug. 2008, pp. 61-71., doi:10.1007/s11302-007-9093-8.

(56) References Cited

OTHER PUBLICATIONS

Jin, X, et al. "Inosine Binds to A3 Adenosine Receptors and Stimulates Mast Cell Degranulation." Journal of Clinical Investigation, vol. 100, No. 11, Jan. 1997, pp. 2849-2857, doi:10.1172/jci119833.

Kim, Hea Ok, et al. "Selective Ligands for Rat A3 Adenosine Receptors: Structure-Activity Relationships of 1,3-Dialkylxanthine 7-Riboside Derivatives." Journal of Medicinal Chemistry, vol. 37, No. 23, 1994, pp. 4020-4030., doi:10.1021/jm00049a021.

Kim, J.-K., et al. "Purinergic Stimulation of Astroblast Proliferation: Guanosine and Its Nucleotides Stimulate Cell Division in Chick Astroblasts." Journal of Neuroscience Research, vol. 28, No. 3, 1991, pp. 442-455., doi:10.1002/jnr.490280318.

Kügelgen, Ivar Von, and Axel Wetter. "Molecular Pharmacology of P2Y-Receptors." Naunyn-Schmiedeberg's Archives of Pharmacology, vol. 362, No. 4-5, May 2000, pp. 310-323., doi:10.1007/s002100000310.

Linden J, Taylor HE., et al. "Molecular cloning and functional expression of a sheep A3 adenosine receptor with widespread tissue distribution". Mol Pharmacol, vol. 44, No. 3, Sep. 1993, pp. 524-532.

Linden J., "Structure and function of A1 adenosine receptors." FASEB J. vol. 5, No. 12, 1991, pp. 2668-2676.

Linden, J., et al. "The Mechanism by Which Adenosine and Cholinergic Agents Reduce Contractility in Rat Myocardium. Correlation with Cyclic Adenosine Monophosphate and Receptor Densities." Circulation Research, vol. 56, No. 5, Jan. 1985, pp. 728-735., doi:10.1161/01.res.56.5.728.

Middlemiss, Pamela J., et al. "Extracellular Guanosine and Guanosine-5'-Triphosphate Increase: NGF Synthesis and Release from Cultured Mouse Neopallial Astrocytes." Brain Research, vol. 677, No. 1, 1995, pp. 152-156., doi:10.1016/0006-8993(95)00156-k.

Molz, Simone, et al. "Neurotoxicity Induced by Glutamate in Glucose-Deprived Rat Hippocampal Slices Is Prevented by GMP." Neurochemical Research, vol. 30, No. 1, 2005, pp. 83-89., doi:10.1007/s11064-004-9689-0.

Moro, Stefano, et al. "Combined Target-Based and Ligand-Based Drug Design Approach as a Tool To Define a Novel 3D-Pharmacophore Model of Human A3 Adenosine Receptor Antagonists: Pyrazolo[4,3-e]1,2,4-Triazolo[1,5-c] Pyrimidine Derivatives as a Key Study." Journal of Medicinal Chemistry, vol. 48, No. 1, 2005, pp. 152-162., doi:10.1021/jm049662f.

Nedden, Stephanie Zur, et al. "HIF-1 Alpha Is an Essential Effector for Purine Nucleoside-Mediated Neuroprotection against Hypoxia in PC12 Cells and Primary Cerebellar Granule Neurons." Journal of Neurochemistry, vol. 105, No. 5, 2008, pp. 1901-1914., doi:10.1111/j.1471-4159.2008.05275.x.

O'dowd, Brian F, et al. "Cloning and Chromosomal Mapping of Four Putative Novel Human G-Protein-Coupled Receptor Genes." Gene, vol. 187, No. 1, 1997, pp. 75-81., doi:10.1016/s0378-1119(96)00722-6.

Okada, Tetsuji, et al. "Activation of Rhodopsin: New Insights from Structural and Biochemical Studies." Trends in Biochemical Sciences, vol. 26, No. 5, 2001, pp. 318-324., doi:10.1016/s0968-0004(01)01799-6.

Palmer, T.m., and G.I. Stiles. "Adenosine Receptors." Neuropharmacology, vol. 34, No. 7, 1995, pp. 683-694., doi:10.1016/0028-3908(95)00044-7.

Pettifer, Kathleen M., et al. "Guanosine Protects SH-SY5Y Cells against β-Amyloid-Induced Apoptosis." NeuroReport, vol. 15, No. 5, 2004, pp. 833-836., doi:10.1097/00001756-200404090-00019.

Pettifer, Kathleen M., et al. "MPP-Induced Cytotoxicity in Neuroblastoma Cells: Antagonism and Reversal by Guanosine." Purinergic Signalling, vol. 3, No. 4, Mar. 2007, pp. 399-409., doi:10.1007/s11302-007-9073-z.

Rathbone, Michel P., et al. "Systemic Administration of Guanosine Promotes Functional and Histological Improvement Following an Ischemic Stroke in Rats." Brain Research, vol. 1407, 2011, pp. 79-89., doi:10.1016/j.brainres.2011.06.027.

Rathbone, Michel P., et al. "Trophic Effects of Purines in Neurons and Glial Cells." Progress in Neurobiology, vol. 59, No. 6, 1999, pp. 663-690., doi:10.1016/s0301-0082(99)00017-9.

Ridge, Kevin D., et al. "Folding and Assembly in Rhodopsin." Journal of Biological Chemistry, vol. 274, No. 30, 1999, pp. 21437-21442., doi:10.1074/jbc.274.30.21437.

Schmidt, André Prato, et al. "Guanosine and GMP Prevent Seizures Induced by Quinolinic Acid in Mice." Brain Research, vol. 864, No. 1, 2000, pp. 40-43., doi:10.1016/s0006-8993(00)02106-5.

Schmidt, André Prato, et al. "Intracerebroventricular Guanine-Based Purines Protect Against Seizures Induced by Quinolinic Acid in Mice." Neurochemical Research, vol. 30, No. 1, 2005, pp. 69-73., doi:10.1007/s11064-004-9687-2.

Soares, Félix A, et al. "Anticonvulsant Effect of GMP Depends on Its Conversion to Guanosine." Brain Research, vol. 1005, No. 1-2, 2004, pp. 182-186., doi:10.1016/j.brainres.2004.01.053.

\* cited by examiner

RT-PCR using GPR22 primers showing GPR22 gene expression in S2 cells following transfection pErk1/2 pAkt

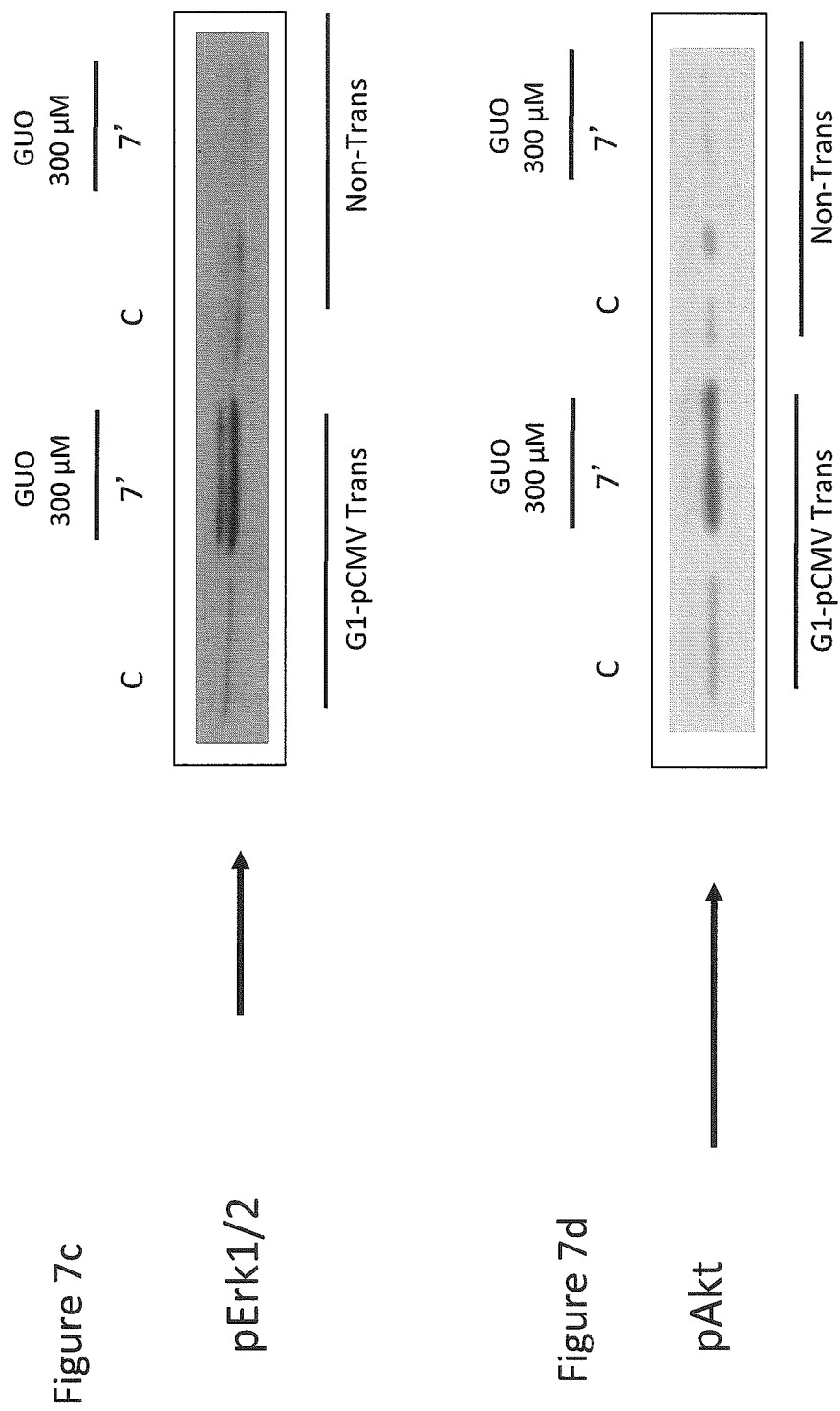

Figure 8

NNNNNNatTGTGgaaacwwcmmtGGTGAGCmmAAAAGGGCCCATAAAGCAAACAGGGAACAGGGGG
AATACCAAACTGCTCCAAAAGAATGTGTTTTTCTCCTGTTCTGAAATCAACATGCAGTCTGA
ATCAAACGTCACGGTGCGAGATGACATTGAGGACATCGATACCAATGTACCAACCACTGTC
ATACCCATTAAGCTTTCAAGTGTCTCTCACTGGATTTCTCATGTTAGAAATTGTGCTGGGCTT
GGTAGCAACCTTACGCGTACTTACTGCATGAAATCCAACTTAATCAGCTCTGTCAGT
AACATTATCACAATGATCTCCATGGTACTGATGTAATAATCTGTGTGGGATGTATCCTCTAAC
CATAGTGATCCTCGCTCTGGAGAGGAACACTGCTCTCATCTGCTGTTCCACGAAGC
TTGTGTTTCTTTTGCAAGTGTTTCCACAACAGAATTCAACGTTTTGCTATTACTCTGGACAGATAT
GACATCTCTGTAAAACTGCAAATGGGCAGAGCTGTGATGCATGAC
GTCCATTGGATTTTCTTCTTCCTGATTCCCTCATTGAAGTCAATTTTTCAGCC
TTCAAAGTGGAAATGCGTGGGAAACACTGCTGTGTCACAAGTGCACAAGTGAGTACTA
CACTGAGCTCGGATGTACTATCACCCTCCTAGTTCAAGATCCCCATCTTCTTCTTCACAGTTATC
GTGATGCTGATCACATACCAAGATACTCCAAGGCTCTTAAATCCGGATAGGCACTAGATTCT
CAACAGGGCCAGAgAAGAAAGCCCGGaGGGAgGGAGGACAATCTCTCTAACCACACATGAGACCA
CAGACATGTCGCAAGCAGTGGGTGGGAGGAAATGTCGTATTGNGTNANNACTTCAGTTTCTG
TANNTNGCCCTCCGCNANCCNTGAAACGACACCGGGAACGACNANNGAGCANAAGANTC
TCAAANGTCNTTANTGATNNTTNNNNNTTTCTNNCTNTGNNNNCANTTCNGTTTAATNCN
NCNTTTATGTTNGNCCNNNNANNNANANANNGGNTCNNNNNNTNNGNNTNNGNN
NACNNNNTNNNCNNCNNNNNNNANAANNAAGNNTNAANNTNAANNNAAANNANT
NNNNNTNNNNNNNANCNNNNN

Figure 9

```
NANGNNCCNNNNNNNNNNNNGANNNNNNNTNCNANANNNNNNANNNA
NNNNNNTNNATNNANNNNNNNNNNNNNNNNNNNNNCAANGNNNNNNTN
NNNNTAGCTTCNNNNNNNNNNNNGATTNCNNNTNNANNNNNGGGNTGGNNNGN
NNTNCGNACNGNACTNNNGCATNAANNCNANTATCAGNTNNTCAGTACATTNNNCNAN
NAATNNCATGNACTTGATGNNNNATCNNNNTGGANGNATTCCTNTAACCATAGNNGATNNT
CTGCTCTCACTGGAGAGGANNACTGCTNTCTGCTGTTNCNNCGAAGCTNGTGTTCNTT
TGCAAGTGTTCCACAGCAATNAACGTTTGCTATACTCTGACAGATATGACATCTGT
AAAACCTGCAAATCTGACAATGGGCAGTGATGCAATTTTCAGCCTTCAAAGTGG
TTTTCTTCTTCTCCTGATTCATTCCNTCATTGAAGTCAATTTTCAGCCTTCACACTGAGCTC
AAATGCGTGGAAACAACAGATCTGAAGCACAAGTAAGTACTACACTGTGAGCTC
GGGATGTACTATCACCCTAGTCCAGATCCCATCTCTTCTCACAGTTATCGTGATGCTGA
TCACATACACCAAGATACTCCAGGTCTTAATATCCGGATAGGCACTAGATTCTCAACAGGCC
AGAAGAAGCCCGGAAGAAAAAGACAATCTCTAACCACACATGAGACCACAGACAT
GTCGCAAAGCAGGTGGGAAATGTCGTATTGGTGTGAAACTTCAGTTTCTGTAATAAT
TGCCCTCCGGGAGCCGTGAAACGACACCGGAAACGAGAGGGCAGAAAAGAGTCTT
CAAAATGTCGTTATTGATATTCTACATTCTCGTTGGACACCAATTCTGTTTAAATA
CCACCATTTATGTTTAGCCCAAGTGACCTTTAGTAAAATTAAGATTGTGTTCTCTAGTCAT
GGCTTATGGAGCAACTATATCCTCTGTATGCATTCACCAGACAAAATTCAAAAG
GTCTTAAAAGTAAGATGAAGGCGAGTGTTCCATAGTTGAAGCTGATCCATGCCTAAT
AACGCTGTATACAACTCATGGATAGATCCTAAAGACAAAAAGGTTACCTACGAAGA
CAgkkAAATAAGAgagAAaNNN
```

Western blot using antibody against GPR22 (G1) receptor showing GPR22 protein expression in S2 cells following transfection

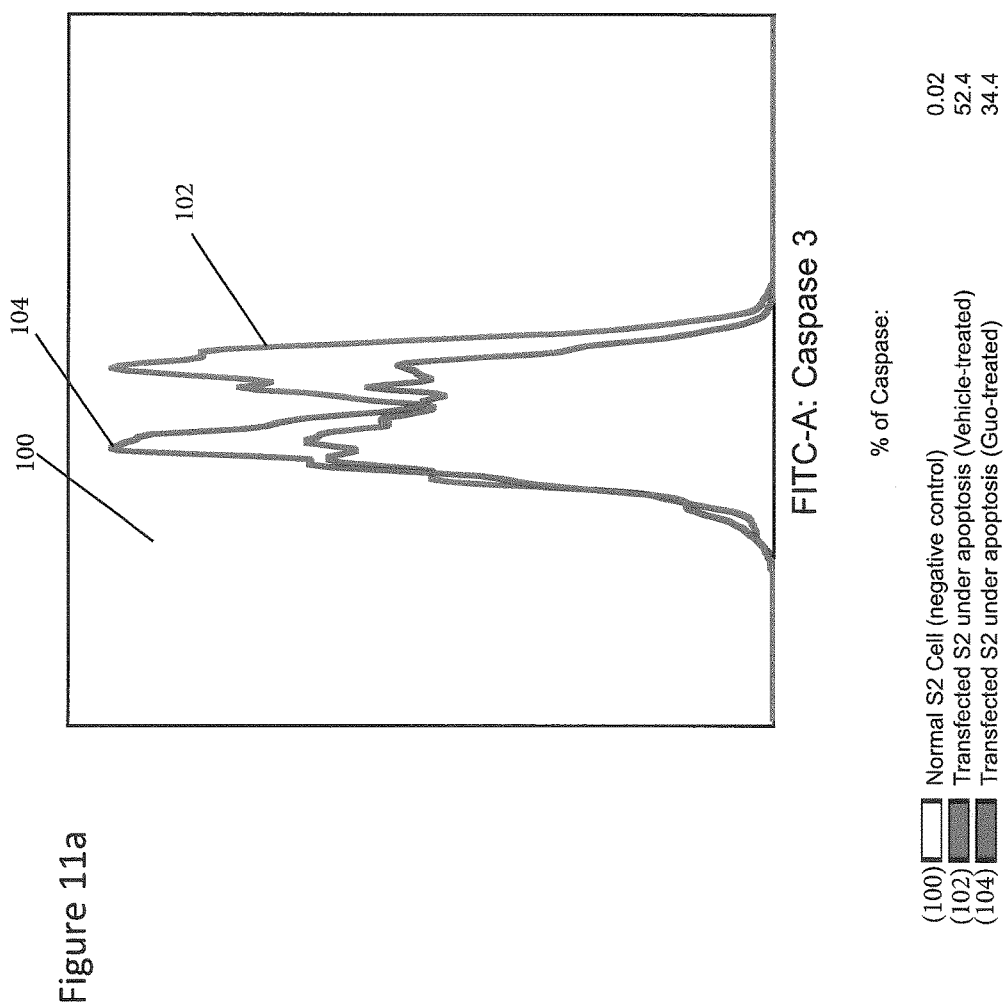

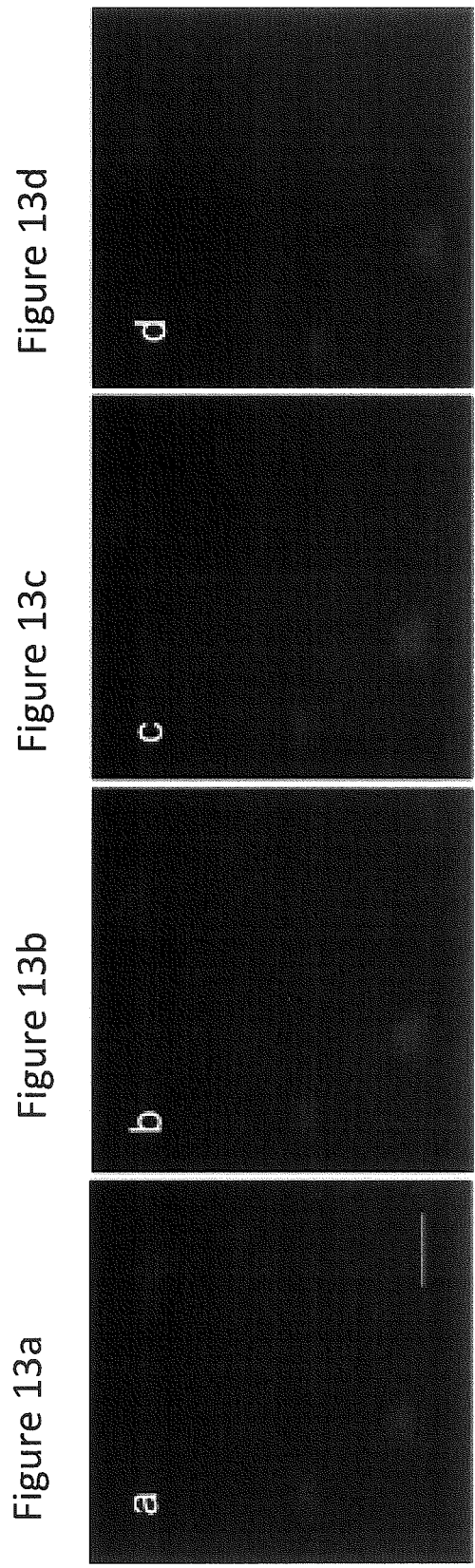

G-PROTEIN-COUPLED-RECEPTOR-22-TRANSFORMED CELL LINES AND METHODS OF USE THEREOF TO IDENTIFY BINDING COMPOUNDS

RELATED APPLICATIONS

The present application is a U.S. Continuation application which claims benefit of priority to International Patent Application serial number PCT/CA2015/050326 entitled "G-Protein Couple Receptor 22 Transformed Cell Lines and Uses Therefor", filed Apr. 20, 2015 which in turn claims benefit of priority to U.S. Provisional Patent Application Ser. No. 61/984,618 entitled "G-Protein Coupled Receptor 22 Transformed Cell Lines And Uses Therefor", filed Apr. 25, 2014 and, U.S. Provisional Patent Application Ser. No. 61/985,373 entitled "G-Protein Coupled Receptor 22 Transformed Cell Lines And Uses Therefor", filed Apr. 28, 2014, the subject matter of which are herein incorporated by reference.

SEQUENCE LISTING

The instant application contains a Sequence Listing which has been submitted electronically in ASCII format and is hereby incorporated by reference in its entirety. Said ASCII copy, created on Jan. 3, 2017, is named 0588_1001_SL.TXT and is 26,963 bytes in size.

TECHNICAL FIELD

The present disclosure relates to transfected cell and cell lines transformed to express G-Protein Coupled Receptor 22 and uses therefor.

BACKGROUND

Extracellular guanosine, like adenosine, has been shown to have a plurality of physiological effects both in vitro and in vivo. It affects the growth, differentiation and survival of various cells (Di Iorio P, Benfenati et al. 2004, 2006; Ballerini et al., 2006; Tavares et al., 2005; Molz et al., 2005, Rathbone et al., 2008). Guanine-based purinergic signalling has been particularly investigated in the nervous system. For example, exogenously added guanosine stimulates the division of certain cells in culture including astrocytes, fibroblasts and certain tumour cells, including brain tumour cells (Rathbone et al., 1990; Kim et al., 1991; Ciccarelli et al., 2000; Su et al., 2009; 2010; 2013; Jiang et al., 2006; Rathbone et al. NNNA 2008). It promotes differentiation of fetal neurons (Rathbone et al., 1999; 2008) and PC12 cells, stimulates outgrowth of nerve processes (neurites) (Gysbers and Rathbone, 1992; 1996; Bau et al., 2005; Di Iorio et al., 2002). Guanosine also prevents apoptosis in astrocytes induced by several stimuli (Pettifer et al., 2004; 2007; Jiang et al., 2007; Su et al., 2009). Furthermore, Guanosine has been shown to protect the CNS from insults such as hypoxia-ischemia (Moretto et al., 2009; Thauerer et al., 2012; Thomazi et al., 2008; zur Nedden et al., 2008), stroke (Chang et al., 2008; Connell et al., 2013; Rathbone et al., 2011), spinal cord injury (Jiang et al., 2008a; Jiang et al., 2007; Jiang et al., 2003a; Sam, 2004), and seizure (Schmidt et al., 2005; Schmidt et al., 2000; Soares et al., 2004), and Parkinson's Disease (Giuliani et al., 2012; Su et al., 2009).

Extracellular guanosine is known to stimulate the synthesis and release of several growth factors from cells, which promotes, for example, astrocyte proliferation (Rathbone et al., 1990; Kim et al., 1991; Ciccarelli et al., 2000), partly by stimulating small numbers of microglia in the astrocyte cultures to produce soluble factors, such as IL-1 (Ciccarelli et al., 2000). Additionally, guanosine promotes the synthesis and release of several potentially neuroprotective trophic factors from a variety of cells, including nerve growth factor (NGF) from astrocytes (Middlemiss et al., 1995) as well as basic fibroblast growth factor (FGF/FGF-2) (Su et al., 2009) and transforming growth factor-$\beta$ (TGF-$\beta$) (Di Iorio et al., 2001). It has been recently shown that exogenous Guanosine can increase intracellular cyclic GMP concentrations through activation of the enzymes hemeoxygenase-1 and hemeoxygenase-2 (HO-1 and HO-2) (Bau et al., 2005).

In some cases guanosine produces its effects by entering cells and interacting with an NGF-dependent protein kinase (Jiang et al., 2006) and under certain circumstances, guanosine acts synergistically with certain growth factors, such as NGF to produce its effects. Guanosine has also been shown to promote the release of adenosine from cells (Ciccarelli et al., 2000); however, most of the effects of guanosine are different from those of adenosine and cannot be explained by adenosine release (Di Iorio et al., 2002).

To date the mechanism through which guanosine exerts its biological effect remains unclear. Many effects of extracellular purine nucleosides and nucleotides are mediated through G-Protein Coupled purine receptors—'purinoceptors' (Burnstock G., 2007) that have common structural features. Preliminary evidence for the existence of a high-affinity binding site, specific for guanosine in rat brain membranes (Traversa U., et al., 2002; Traversa et al., 2003; Volpini et al., 2011), analogous to the adenine receptor (Wengert M et al., 2007) has been obtained. Accordingly, it is believed that guanosine is responsible for the activation of a number of intracellular signalling pathways. These intracellular signalling pathways, for example, result in the elevation of cAMP in rat brain membranes (Traversa et al., 2003) and in primary stem cells (Su et al., 2013), PI3kinase/Akt/PKB and mitogen-activated protein kinase and ERK1/2 phosphorylation which are characteristic responses of activated G-Protein Coupled Receptors (Di Iorio P et al., 2001; Pettifer et al, 2007; Traversa U., et al., 2002; Ballerini et al., 2006; Di Iorio et al., 2004; Giuliani et al., 2012). The addition of exogenous guanosine to cultured mouse primary astrocytes also leads to the elevation of intracellular calcium concentrations, although it is unclear whether this is mediated via the putative Guanosine receptor (Chen et al., 2001). Interestingly, the effects of guanosine on the production of trophic factors by astrocytes and the anti-apoptotic effects of guanosine are sensitive to pertussis toxin, an inhibitor of Gi and Go coupled G-protein Receptors (Fields T A and Casey P J, 1997), and are not inhibited by inhibitors of nucleoside or nucleobase transport, which lends support for the hypothesis that guanosine acts extracellularly. Furthermore, rat brain membranes have been shown to have high affinity cell surface binding sites specific for guanosine>>inosine that do not bind adenosine (Traversa U., et al., 2002).

On the basis of pharmacological and molecular cloning studies, the International Union of Pharmacology Committee on Receptor Nomenclature and Drug Classification (NC-IUPHAR) has subdivided purinoceptors into two major classes: adenosine (P1) receptors and nucleotide (P2) receptors (Fredholm et al., 2001; Abbracchio and Burnstock, 1994). Four subtypes of adenosine receptors have been identified: $A_1$, $A_{2A}$, $A_{2B}$, and $A_3$. Each has a unique tissue distribution, signal transduction mechanism, and ligand affinity. All adenosine receptor subtypes are coupled to heterotrimeric G proteins. Activation of $A_1$ or $A_3$ subtypes inhibits adenylate cyclase activity, whereas activation of $A_2A$ and $A_2B$ subtypes stimulates adenylate cyclase activity. Additionally, $A_1$ and $A_3$ subtypes are coupled to other signal transduction pathways, including phosphoinositol hydrolysis and potassium channels (Ramkuran et al., 1993; Linden, 1991).

In addition to their different effects, these receptor subtypes can also be distinguished by the potency order of a series of agonists and antagonists (Palmer and Stiles, 1995). Adenosine is the preferred endogenous agonist at all adenosine receptors. But the naturally-occurring purine inosine, for which no unique receptor has been identified, binds to, and activates $A_3$ receptors (Jin et al., 1997; Linden et al., 1985), producing immunomodulatory and neuroprotective effects (Gomez and Sitkovsky, 2003; Hasko et al., 2004). $A_3$ receptor subtypes exhibit the lowest degree of amino acid sequence identity either with different species homologues (Palmer and Stiles, 1995; Fredholm et al., 2001) or with other adenosine receptor subtypes, resulting in unique pharmacological properties (Linden et al., 1993).

P2 receptors are further divided into P2X ligand-gated ion channels, which are activated solely by ATP, and G-Protein Coupled P2Y receptors which are activated both by extracellular adenine and uracil nucleotides. Eight P2Y receptors (P2Y1, 2, 4, 6, 11, 12, 13, 14) have been cloned from mammalian tissues (Abbracchio 2003, Zhang 2002, North 2002, Fredholm, 1997). P2Y receptor activation stimulates phosphoinositol hydrolysis. Additionally, activation of P2Y12, 13, 14 receptors inhibits adenylyl cyclase whereas P2Y11 activation stimulates this enzyme (von Kugelgen and Wetter, 2000).

P1 and P2Y purinoceptors are integral membrane proteins that belong to the class A, rhodopsin-like, G-Protein Coupled Receptor (GPCR) superfamily. These purinoceptors are predicted to share a conserved molecular architecture consisting of seven hydrophobic transmembrane domains (TMDs), which span the plasma membrane, connected by three intracellular and three extracellular loops (Watson et al., 1994).

It is difficult to extract and crystallise GPCRs. Indeed, only the rhodopsin receptor has been crystallised and studied by X-ray diffraction. However, it has been possible to predict the tertiary structure of other GPCRs based on the atomic co-ordinates of the rhodopsin receptor. Since P1 and P2Y receptors have not been crystallised, an understanding of how purinoceptors bind their cognate ligands is based on modelling studies combined with site-directed mutagenesis. GPCRs have low amino acid sequence homology. However, there are several highly conserved key amino acid residues which may be essential for either the structure or function of the receptors. As in other receptor families, similarity between sequences of the P1 or P2Y receptor family is greatest in the hydrophobic TMDs.

Certain well-conserved amino-acid residues of the P2Y receptor subfamily have been used to identify and clone new P2Y receptors (Chambers et al., 2000; Communi et al., 2001; Joost and Methner et al., 1997; Jiang et al., 1997). In contrast, no orphan receptor related to the P1 receptor subfamily has been identified. However, mutational data have identified some amino acid residues important for ligand binding to adenosine receptors (Fredholm et al., 2001).

This background information is provided to reveal information believed by the applicants to be of possible relevance. No admission is necessarily intended, nor should it be construed, that any of the preceding information constitutes prior art.

SUMMARY

The following presents a simplified summary of the general inventive concepts described herein to provide a basic understanding of some aspects of the invention. This summary is not an extensive overview of the invention. It is not intended to restrict key or critical elements of the invention or to delineate the scope of the invention beyond that which is explicitly or implicitly described by the following description and claims.

Based on the evidence of G-Protein Coupled Receptors specific for adenosine and the suspected existence of a receptor for guanosine as well as the intracellular responses of exogenously added guanosine to tissue cultures, inter alia, an investigation was undertaken to locate motifs in the primary sequence of the TMDs of P1 adenosine receptors, which may be important for the binding of guanosine. Accordingly, adenosine $A_3$ receptor-like sequences among orphan receptors were searched given that $A_3$ receptors bind inosine as discussed in more detail below. The sequences of orphan receptors were analyzed to identify similar motifs. Through such studies, G-Protein Coupled Receptor 22 (GPCR22—SEQ. ID NO: 3) was identified as a possible G-Protein Coupled Receptor able to bind guanosine. Surprisingly, further research verified GPCR22 as a novel guanosine binding receptor. Guanosine was shown in further studies, discussed below, to make functional binding to GPCR22 when expressed in cells which do not normally express the GPCR22 receptor. Additionally, Guanosine, binding to GPCR22 was also shown, using biochemical, pharmacological and physiological techniques, to elicit cellular effects in such cells.

It would be desirable to identify a method useful for identifying guanosine analogues which may act as agonists, partial agonists and inverse agonists on a G-Protein Coupled Receptor able to bind guanosine. Furthermore, in some embodiments it would be desirable to provide a means for identifying various cell types expressing a receptor able to bind guanosine.

In one aspect there is provided a transformed cell line expressing a non-endogenous G-Protein Coupled Receptor. The transformed cell line is proliferated from a host cell having been transformed to express a cell-surface G-Protein Coupled Receptor able to bind guanosine and guanosine analogs. In some embodiments, the host cell is transfected with a recombinant cDNA sequence coding for an amino acid sequence of the cell-surface G-Protein Coupled Receptor able to bind guanosine and guanosine analogs. In preferred embodiments, the amino acid sequence corresponds to GPCR22. Furthermore, in some embodiments, the recombinant cDNA sequence comprises SEQ. ID NO: 1 or SEQ. ID NO: 2. In some embodiments, the amino acid sequence comprises SEQ. ID NO: 3. In preferred embodiments, the host cell is a *Drosophila* Schneider 2 cell or a human astrocytoma 1321N1 cell.

In another aspect, there is provided a method for producing the transformed cell line as defined above. The method comprises transfecting the host cell with an expression vector, where the expression vector comprises a polynucleotide and the polynucleotide comprises a nucleotide sequence encoding for a polypeptide comprising the amino acid sequence of SEQ. ID NO. 3.

In yet another aspect, there is provided a method for identifying a compound bindable to a selective guanosine responsive G-Protein Coupled Receptor. The method comprises contacting one or more candidate compounds with a host cell transformed to express a receptor comprising an amino acid sequence comprising SEQ. ID NO: 3; and measuring the ability of the one or more candidate compounds to stimulate or inhibit a cellular function associated with said receptor. In some embodiments, the amino acid sequence is encoded by DNA comprising SEQ. ID NO: 1 or SEQ. ID NO: 2. Furthermore, in some embodiments, the cellular function evaluation comprises measuring apoptosis regulation, intracellular calcium mobilization, intracellular protein phosphorylation or a second messenger intracellular pathway activation. In some embodiments, the host cell is a Drosophila Schneider 2 cell or a human astrocytoma 1321N1 cell. Furthermore, in some embodiments, the one or more candidate compounds may be an agonist, a partial agonist or an inverse agonist of the receptor.

In another aspect, there is provided a method for transforming a host cell to express a guanosine bindable G-Protein Coupled Receptor. The method comprises transfecting a host cell with an expression vector, where the expression vector comprises a polynucleotide sequence comprising SEQ. ID NO: 1 or SEQ. ID NO: 2, encoding for a polypeptide comprising an amino acid sequence comprising SEQ. ID NO: 3; and wherein the host cell under the appropriate culture conditions, produces a polypeptide comprising the amino acid sequence of SEQ. ID NO: 3. In preferred embodiments, the polypeptide comprising SEQ. ID NO: 3 corresponds to GPCR22 and is expressed at the cell surface. In preferred embodiments, the host cell is a Drosophila Schneider 2 cell or a human astrocytoma 1321N1 cell.

In yet another aspect, there is provided a G-Protein Coupled Receptor capable of binding guanosine or analogs thereof. In some embodiments the G-Protein Coupled Receptor has an amino acid sequence having at least 70% homology to SEQ. ID NO: 3. In some embodiments the G-Protein Coupled Receptor has an amino acid sequence having at least 80% homology to SEQ. ID NO: 3. In some embodiments the G-Protein Coupled Receptor has an amino acid sequence having at least 90% homology to SEQ. ID NO: 3. In some embodiments the G-Protein Coupled Receptor has an amino acid sequence having at least 95% homology to SEQ. ID NO: 3. In some embodiments, the G-Protein Coupled Receptor capable of binding guanosine or analogs thereof, has an amino acid sequence corresponding to SEQ. ID NO: 3.

In another aspect, there is provided a method for identifying a cell having a G-Protein Coupled Receptor able to bind guanosine or analogues thereof. The method comprises extracting DNA from a population of subject cells, executing a polymerase chain reaction (PCR) technique on said DNA extracted from said population of subject cells using a forward primer corresponding to SEQ ID NO: 5. and a reverse primer corresponding to SEQ. ID NO: 6 and analyzing the PCR product resultant therefrom.

In still yet another aspect, there is provided a transformed cell line expressing a non-endogenous G-Protein Coupled Receptor capable of binding guanosine or analogues thereof wherein the non-endogenous G-Protein Coupled Receptor has a guanosine or analogue thereof binding domain located in transmembrane domain 6, where the binding domain comprises SEQ. ID NO: 7 or SEQ ID NO: 8. In preferred embodiments, the transformed cell line is from a Drosophila Schneider 2 cell or a human astrocytoma 1321N1 cell transfected to express GPCR22.

Other aims, objects, advantages and features of the invention will become more apparent upon reading of the following non-restrictive description of specific embodiments thereof, given by way of example only with reference to the accompanying drawings.

BRIEF DESCRIPTION OF THE FIGURES

In order that the invention may be better understood, exemplary embodiments will now be described by way of example only, with references to the accompanying drawings, wherein:

FIG. 7c is a photograph of a Western Blot showing Erk 1/2 phosphorylation by guanosine in 1321N1 human astrocytoma cells and 1321N1 human astrocytoma cells transfected with GPCR22 DNA;

FIG. 7d is a photograph of a Western Blot showing Akt phosphorylation by guanosine in 1321N1 human astrocytoma cells and 1321N1 human astrocytoma cells transfected with GPCR22 DNA;

FIG. 8 shows the sequence confirmation results of GPCR22-pMT-GPCR22-Forward GPCR22 transfection in Drosophila Schneider 2 transformed cells (SEQ ID NO: 16);

FIG. 9 shows the sequence confirmation results of GPCR22-pMT-GPCR22-Reverse GPCR22 transfection in Drosophila Schneider 2 transformed cells (SEQ ID NO: 17);

FIGS. 13 a to d are fluorescence images showing the effect of guanosine on the level of intracellular $Ca^{2+}$ in GPCR22-transfected *Drosophila* Schneider 2 cells over a time course;

BRIEF DESCRIPTION OF THE SEQUENCES

Figure 1:
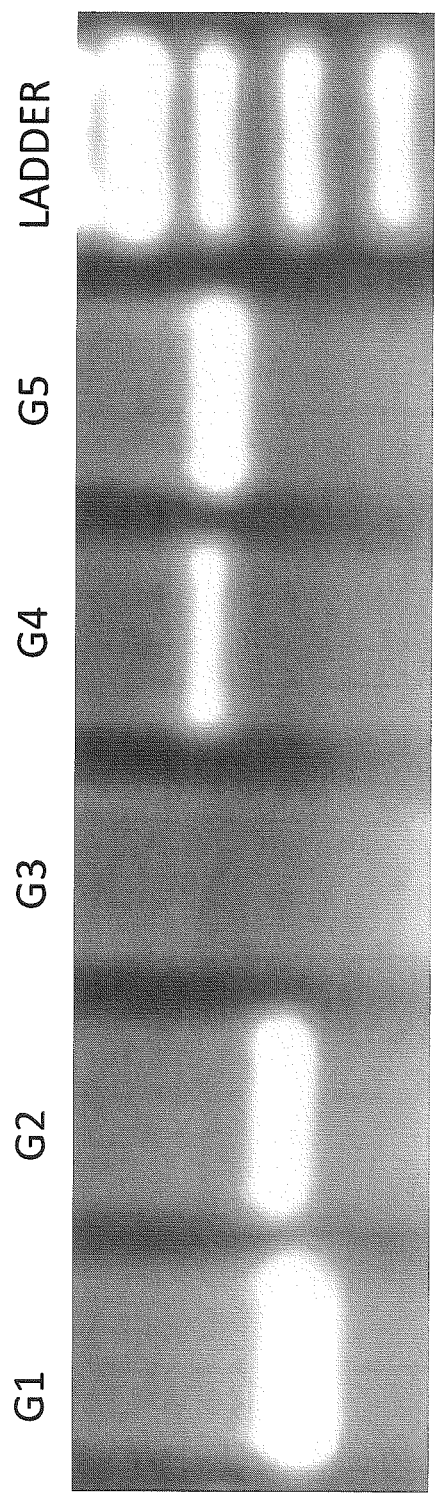
FIG. 1 is a photograph of a gel electrophoresis showing the expression of GPCR22 (G1) determined by real-time PCR in cultured rat astrocytes.

SEQ. ID NO: 1 is an exemplary cDNA polynucleotide sequence having 100% homology to Rat GPCR22 and 97% homology to mouse GPCR22 using the exemplary forward primer of SEQ. ID NO: 5 of the instant disclosure;

SEQ. ID NO: 2 is a cDNA polynucleotide sequence having 100% homology to Rat GPCR22 and 97% homology to mouse GPCR22 using the exemplary reverse primer of SEQ. ID NO: 6 of the instant disclosure;

SEQ. ID NO: 3 is an exemplary amino acid polypeptide sequence corresponding to GPCR22 of the instant disclosure;

SEQ. ID NO: 4 is an exemplary mRNA polynucleotide sequence corresponding to a mouse GPCR22 of the instant disclosure;

SEQ. ID NO: 5 is oligonucleotide sequence corresponding to an exemplary forward primer for GPCR22 of the instant disclosure;

SEQ. ID NO: 6 is oligonucleotide sequence corresponding to an exemplary reverse primer for GPCR22 of the instant disclosure; and SEQ. ID NO: 7 is a polypeptide sequence of an exemplary GPCR22 transmembrane 6 binding domain of the instant disclosure; and SEQ. ID NO: 8 is a polypeptide sequence of an exemplary GPCR22 transmembrane 6 binding domain of the instant disclosure.

DETAILED DESCRIPTION

With reference to the disclosure herein and the appended figures, cell lines transformed to express GPCR22 and a method for identifying guanosine analogues which may be agonists, partial agonists and inverse agonists of GPCR22 are described in accordance with various embodiments of the invention.

Example 1: Identification of the G1 Receptor Using Bioinformatic Approaches

Based on the pharmacological and transductional evidence supporting the existence of the putative G1 receptor, preliminary structural data using bioinformatic approaches was used to identify possible orphan G-Protein Coupled Receptors capable of binding guanosine. Using DNA and Protein databanks, the sequence motifs of the 7 transmembrane segments (TMs) for the adenosine $A_1$, $A_3$, $A_{2a}$ and $A_{2b}$ receptors, which are highly conserved among these receptor subtypes were used to identify possible candidates for guanosine bindable orphan G-Protein Coupled Receptors. Inosine, a purine similar structurally to guanosine, is known to interact with the adenosine $A_3$ receptors, as well as having been shown to bind to the putative G1 binding site in rat brain. Therefore, the sequence for the TMs 3, 5, 6 and 7 of the human adenosine $A_3$ receptors was selected, which constitutes the hydrophobic binding pocket for both, agonists and antagonists (Moro et al., 2005), and screened against the sequences of some of the orphan G-Protein Coupled Receptors (GPCRs) in the databanks. Based on this sequence homology to the human adenosine $A_3$ receptor several orphan GPCRs with potential G1 (guanosine) receptor activity were identified.

Many of the amino acid residues important for ligand binding to ATP or adenosine receptors are located in the sixth TMD (Fredholm et al., 2001). Accordingly, a multiple sequence alignment (Clustal-W program, blosum matrix) and Sequence motif search (http://expasy.org) was used to develop novel patterns within the sixth TMD characteristic of P2Y and P1 receptors.

It was noted that the local sequence: hhx[CS][FY]hPhHhx[RK] is shared among all P2Y sequences reported at SwissProt and GeneBank databases. This consensus pattern, when scanned against sequence databases, matched only with proteins belonging to P2Y class. However, this pattern also contains residues which are maintained in all metabotropic purinoceptors. In particular at 254, 255, 259 and 261 positions (referring to the numbering of the human P2Y2 receptor) a hydrophobic residue (h) is strictly conserved in all P1 and P2 receptors. The role of these hydrophobic residues is unknown. A Pro residue (at position 261) is also strictly maintained in all metabotropic purinoceptors. This represents one of the most conserved amino acid residues in the GPCR superfamily. Analysis of the crystal structure of the rodhopsin receptor and mutagenesis studies indicates that the corresponding Pro267 plays a critical role in the overall protein conformation (Okada et al., TiBS 2001; Ridge et al., 1999). The function of the [CS] residue, strictly maintained at position 257 in all P2Y and P1 receptors, has never been investigated.

Mutagenesis studies indicate that single substitution of the conserved His-262 and Arg-265 with leucine decreased the potency but not the efficacy of ATP and UTP on the P2Y2 receptor, suggesting that these amino acid residues are mainly involved in the ligand binding (Erb et al., 1995). Molecular modelling studies also indicate that His-262 and Arg-265 interact with negatively charged phosphate residues of ATP (Erb et al., 1995). Arg-265 is always present in P2Y nucleotide receptors except for P2Y1 and P2Y6 in which a Lys residue occurs in an analogous position. Thus a positive charged residue at position 265 seems to be needed for nucleotide binding (Erb et al., 1995; von Kugelgen and Wetter, 2000).

In the TM6 domain, the consensus pattern of P1 receptors is clearly distinct from that of the P2Y. In particular the $A_1$, $A_2A$ and $A_2B$ subtypes are generally characterised by the conserved local motif hhx[CS]WhPhHxxNxhTxF (SEQ ID NO: 9), whereas $A_3$ receptors contain a different consensus pattern hhx[CS]WhPh[CS]hxNxhxxF (SEQ ID NO: 10). The sequence alignment showed that His-262 residue is strictly maintained in P2Y as well as in all $A_1$, $A_2a$ and $A_2b$ receptor subtypes, but not in $A_3$ receptor sequences. Several mutagenesis studies have demonstrated that in $A_1$, $A_2a$ and $A_2b$ subtypes this highly conserved His is involved in ligand binding (Olah et al., 1992; Kim et al., 1994). In the TM6 domain of all $A_3$ adenosine receptors, the His-262 is always replaced by a Ser residue. Mutagenesis studies indicate that Ser-247 of human $A_3$ receptors is not involved in agonist binding but, rather, in that of antagonists (Gao et al., 2002). Although adenosine is the main endogenous agonist at $A_3$ receptors, inosine can also activate them (Jin et al., 1997; Linden et al., 1995; Fredholm et al., 2002), as noted above. The presence of a Ser, instead of His, residue is peculiar to $A_3$ receptors. Whether this His plays a role in inosine binding is unknown.

The alignment also revealed that the Lys/Arg residue (265 in P2Y2), involved in the interaction with charged phosphate residues of ATP and present in all P2Y receptors (Erb et al., 1997), is replaced by an Asn residue in an analogous position (250 $A_3$ and 253 $A_2A$) in all P1 subtypes. Mutational studies indicate that this conserved Asn is involved either in receptor-ligand recognition or in maintaining receptor structure (Kim et al., 1995; Gao et al., 2002). In contrast to P2Y receptors, a Trp residue (Trp-243 in the human $A_3$ receptor) is rigorously maintained in all P1 sequences. This residue is appears to be needed for activation of the $A_3$ receptor but not for agonist binding (Gao et al., 2002), since substitution of the Trp-243 by a Phe residue impairs the ability of agonists to activate PLC (Gao et al., 2002). A Thr residue (Thr-257 in human $A_1$) is highly conserved in $A_1$, $A_2a$ and $A_2b$ subtypes, distinguishing $A_1$ and $A_2$ from $A_3$ receptor sequences. The consensus residue Phe-262 (in human $A_1$) is unique to the P1 class. No characteristic residue is found at a homologous position in P2Y receptors.

The identification of a specific pattern for the $A_3$ s has been shown to be a good approach to predict ligands for additional $A_3$-related orphan receptor. This pattern was built so as to contain residues that are of the P1 receptor subfamily, especially those that can form plausible intermolecular interaction with the ligand class (inosine). Among orphan GPCRs, only one met the above-note characteristics as discussed below.

Therefore, a consensus pattern of hhx[CS]WxPh[CS]hxNxhxxF (SEQ ID NO: 11), was defined that contained residues specific for the $A_3$ subtype of P1 receptors, for which inosine as well as adenosine is an agonist. When scanned against sequence databases the consensus pattern matched only with $A_3$ receptor subtypes. However when the consensus sequence was shortened to hhx[CS]WxPh[CS]hxN, the pattern also matched the orphan G-Protein Coupled Receptor 22 (GPCR22) from human, rat and mouse.

By comparing the amino acid sequences of the $A_3$ receptors against that of GPCR22, it was surprisingly discovered that the overall percentage of identity between adenosine $A_3$ receptors and GPCR22 is low, being about 13%. However, if only TM6 is considered, the percentage of identity rises to 30%. Therefore, as result of the above analysis, it was determined that there may be a binding domain in TM6 of GPCR22 for guanosine represented by hhx[CS]WxPh[CS]hxN. For example, using the $A_3$ receptor amino acid alignment as a reference, the binding domain may be located beginning at TM6 amino acid residue 239, preceded by two hydrophobic residues at positions 239 and 240, and additional hydrophobic residues at locations 246 and 248. Accordingly, the binding domain may be as follows, where h denotes hydrophobic residues and x denotes unknown amino acid residues: h-239, h-240, x-241, Ser-242, Trp-243, x-244, Pro-245, h-246, Ser-247, h-248, x-249, Asn-250 or h-239, h-240, x-241, Cys-242, Trp-243, x-244, Pro-245, h-246, Cys-247, h-248, x-249, Asn-250, noted below as SEQ. ID NO: 7 and SEQ. ID NO: 8, respectively.

Notably, in addition to strictly conserved residues typical of the P1 receptors, GPCR22 shares a Ser residue analogous to Ser-247 of the human $A_3$ receptor. GPCR22 shares a higher sequence identity with the cholecystokinin-B receptor (34%) (O'Dowd et al., 1997) than with the $A_3$ receptor. Nevertheless, GPCR22 (SEQ. ID NO: 3) shares with $A_3$ receptors residues in TM6 that are specific for P1 receptor subfamily, and which are believed to be likely important in purine nucleoside ligand binding.

These data indicate that GPCR22 may have substrate binding characteristics related to an $A_3$ receptor. Although adenine nucleotides and adenosine are the prototypical purinergic signalling molecules, non-adenine-based purines, including guanosine and inosine, have recently been shown to have important neuromodulatory roles (Soares et al., 2004; Gomez and Sitkovsky, 2003). Moreover, as noted above, a receptor-like cell surface binding site for guanosine has been identified (Traversa et al., 2002; Traversa et al., 2003). Therefore, it was investigated as to whether the orphan receptor GPCR22 is a novel nucleoside receptor.

Based on the above-noted analysis, GPCR22 was selected as a potential candidate for a G-Protein Coupled Receptor capable of binding guanosine, also referred to herein as the G1 receptor, and producing cellular effects.

Example 2: Inhibition of GPCR22 by siRNA in Primary Astrocytes

GPCR22 Expressed in Cultured Rat Astrocytes:

With reference to FIG. 1, RT-PCR experiments showed that GPCR22, the G1 receptor, as also referred to herein, is expressed in cultured rat astrocytes. The primers used for the RT-PCR experiments were GPCR22 forward: CTC ATC TGC TGT TTC CAC GA (SEQ. ID NO: 5) and GPCR22 reverse CGG ATG TTA AGA GCC TGG AG (SEQ. ID NO: 6).

siRNA for GPCR22 Experiments on Cultured Rat Astrocytes:

Transient transfection of siRNAs for the rGPCR22 gene on rat cultured astrocytes and cell extracts were assayed for gene silencing 24 h after transfection was carried out. siRNA duplex specific for the rGPCR22 receptor were designed and chemically synthesized (www.Dharma.com), as well as their non specific control (NSC). Transfection of siRNAs for targeting endogenous genes was carried out using Oligofectamine (Invitrogen, Life Technologies) according to the manufacturer's instruction. Briefly, astrocytes at 60-70% confluence were cultured for 1 day in culture medium without antibiotics. 10 ml siRNA (20 mM) (Dharmacon research, Inc.) were diluted in 175 ml optimem for 5 min at room temperature. In the meantime, 3 ml oligofectamine was mixed in 15 ml optimem for 5 min. RNA interference was performed by mixing diluted oligofectamine and siRNA for 30 min at room temperature and was then added to the cells. The same scheme was performed on other samples using a siRNA-scrambled (NSP=non specific control). Cells were incubated at 37° C. for 24 hours. Twenty-four hours after transfection, the cells were lysed and assayed for gene silencing. The effect of GPCR22 silencing on MAPK and AKT phosphorylation, and cAMP assay was analysed.

Figure 2A:
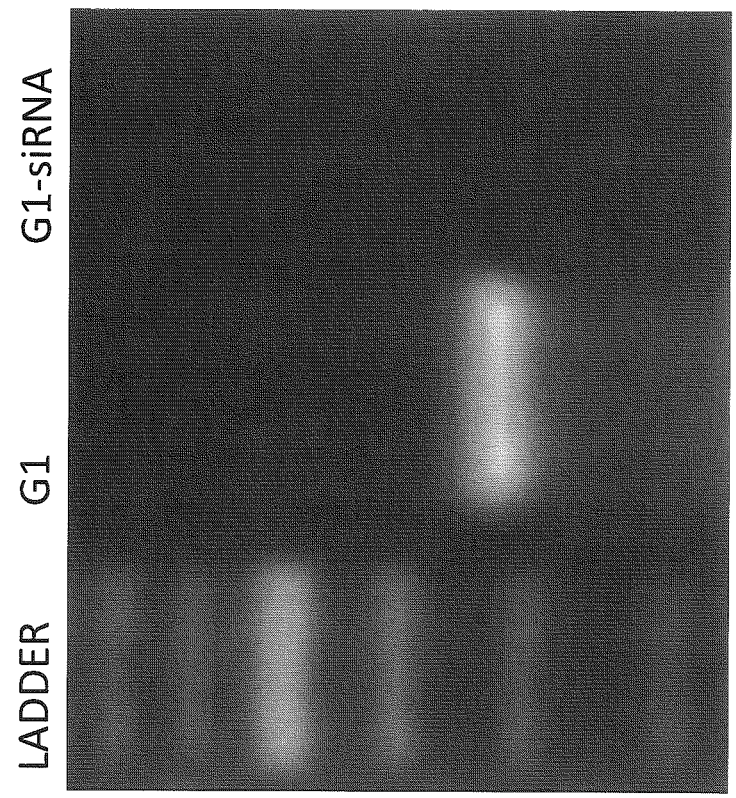
FIG. 2a is a photograph of a gel electrophoresis showing the silencing of GPCR22 (G1) by siRNA determined by real-time PCR in cultured rat astrocytes compared to cultured rat astrocytes not treated with siRNA for GPCR22.
Figure 2B:
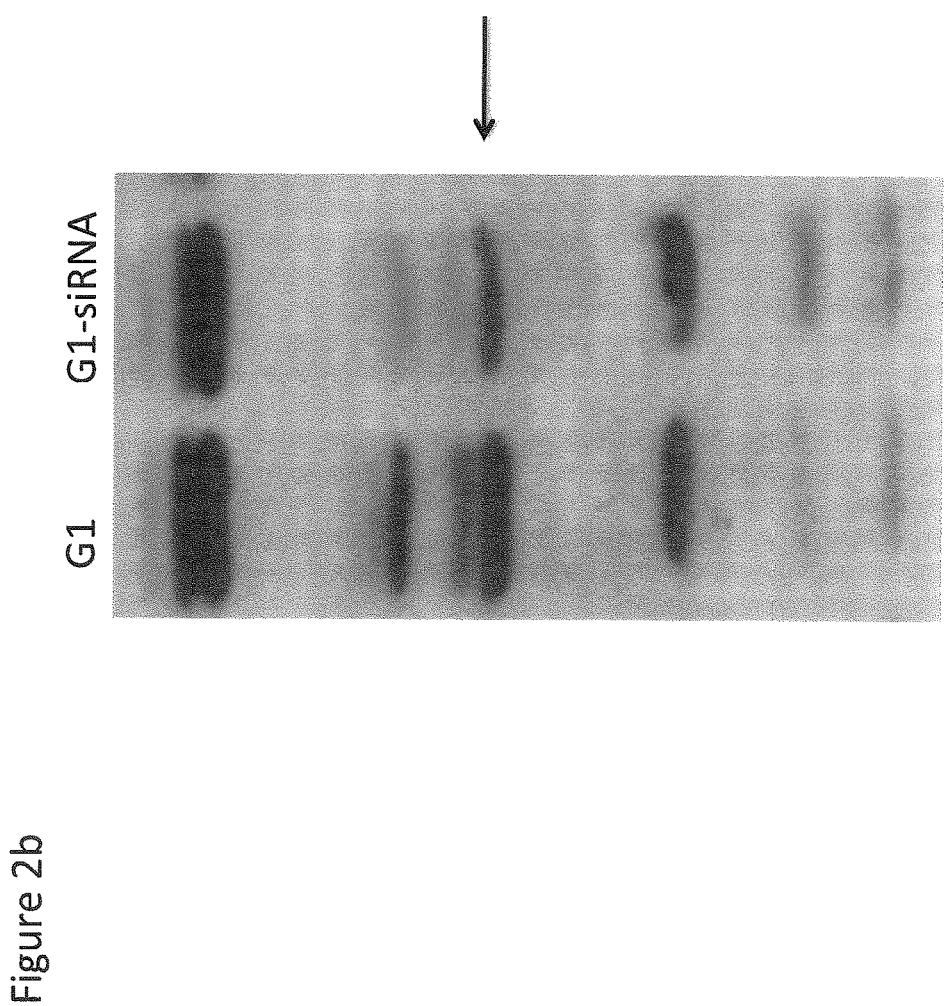
FIG. 2b is a photograph of a Western Blot showing the silencing of GPCR22 protein in cultured rat astrocytes by siRNA.

Using siRNA for GPCR22 in cultured rat astrocytes, the expression of GPCR22 (G1) was shown to be abolished by RT-PCR, as shown in FIG. 2a. FIG. 2a shows the results of RT-PCR for the GPCR22 DNA (G1) in cultured rat astrocytes and cultured rat astrocytes treated with siRNA for GPCR22 (G1-siRNA). Additionally, through Western Blot analysis (FIG. 2b) using a rabbit polyclonal anti-GPCR22 antibody (NovateinBio, SH-A12465, MA, USA) it was shown that the GPCR22 protein expression in cultured rat astrocytes was inhibited by siRNA. Furthermore, in astrocytes, inhibition of GPCR22 by siRNA was shown to abolish both guanosine binding and activation of intracellular signaling by guanosine (data not shown).

Example 3: Transfection of hGPCR22 in 1321N1 Human Astrocytoma Cells

Figure 5:
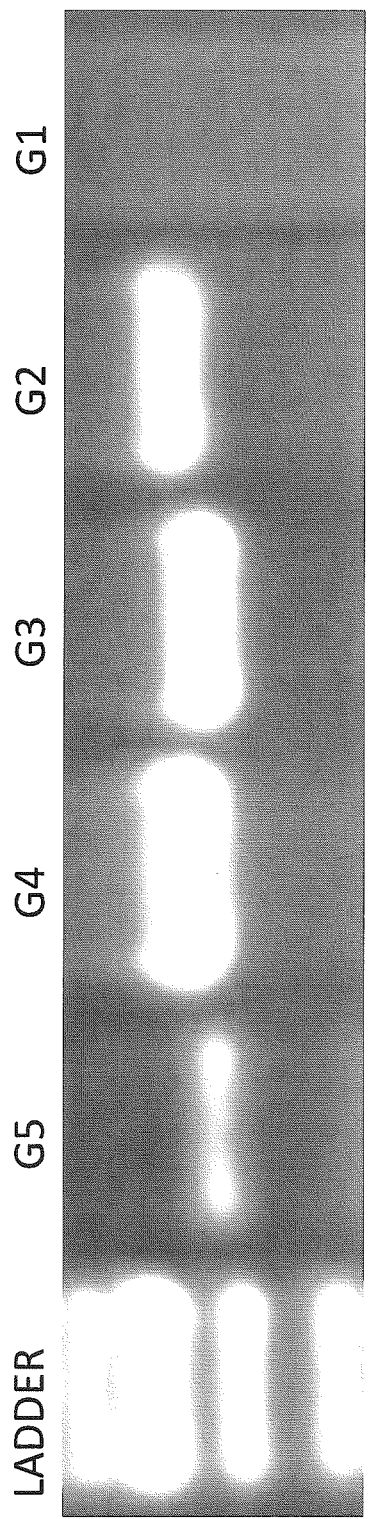
FIG. 5 is a photograph of a gel electrophoresis showing that 1321N1 human astrocytoma cells do not express GPCR22 (G1) as determined by real-time PCR.

GPCR22 is not Expressed in 1321N1 Human Astrocytoma Cells:

With reference to FIG. 5, RT-PCR experiments showed that GPCR22 (G1) is not expressed in 1321N1 human astrocytoma cells. The primers used for the RT-PCR experiments were GPCR22 forward: CTC ATC TGC TGT TTC CAC GA (SEQ. ID NO: 5) and GPCR22 reverse CGG ATG TTA AGA GCC TGG AG (SEQ. ID NO: 6).

Figure 6A:
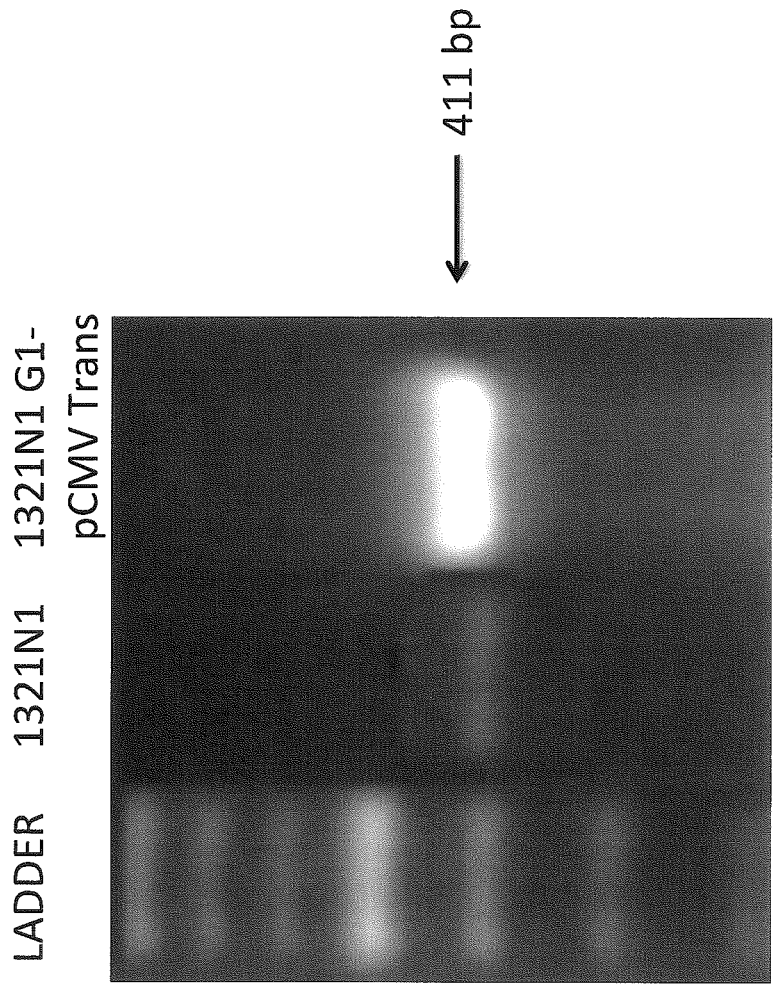
FIG. 6a is a photograph of a gel electrophoresis showing the transfection of GPCR22 (G1) DNA into 1321N1 human astrocytoma cells determined by real-time PCR.
Figure 6B:
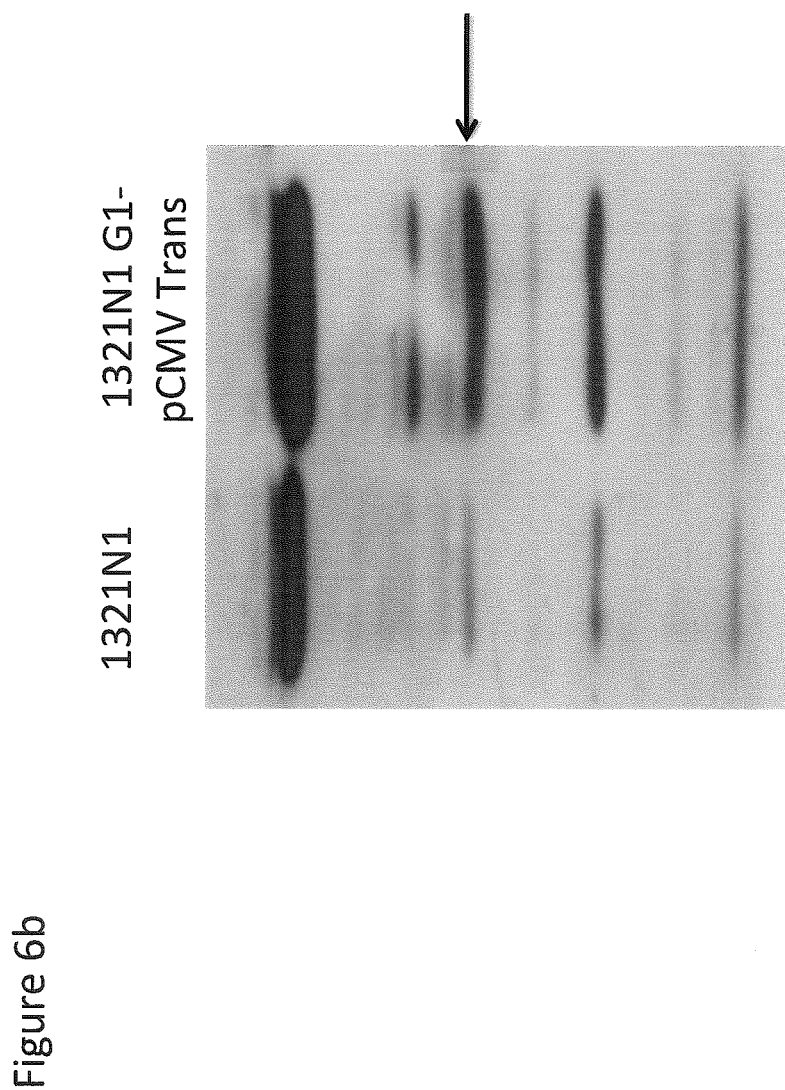
FIG. 6b is a photograph of a Western Blot showing the expression of GPCR22 protein following GPCR22 (G1) DNA transfection into 1321N1 human astrocytoma cells.

Transient Transfection of hGPCR22 in 1321N1:

A full length cDNA clone of human GPCR22 was provided by Origene Technologies. Transient expression in the 1321N1 cell line was performed using a pCMV expression vector. cDNA fragments present in an expression vector (pCMV) is located downstream of a transcriptional promoter capable of driving heterologous gene expression in a variety of mammalian cells. 1321N1 cell lines were transiently transfected with hGPCR22 cloned into pCMV expression vectors (Invitrogen). DNA transfection was performed by lipofection using Lipofectamine (Life Technologies). Twenty-four hours after transfection, the cells were lysed and assayed. RT-PCR analysis using GPCR22 forward: CTC ATC TGC TGT TTC CAC GA (SEQ. ID NO: 5) and GPCR22 reverse CGG ATG TTA AGA GCC TGG AG (SEQ. ID NO: 6), was used to confirm the transfection of GPCR22 (G1) (labelled "1321N1 G1-pCMV Trans") into 1321N1 cells as shown in FIG. 6a and evidenced by the band at 411 bp. Furthermore, the expression of GPCR22 (labelled "1321N1 G1-pCMV Trans") in 1321N1 cells as compared to non-G1 transfected cells (labelled "1321N1") was confirmed by Western Blot analysis using a rabbit polyclonal anti-GPCR22 antibody (NovateinBio, SH-A12465, MA, USA), as shown in FIG. 6b.

Stable Transfection of hGPCR22 in 1321N1:

It was determined from the above-noted assays that the pCMV vector could not be used for stable transfection. Therefore hGPCR22 was cloned into a pCDNA3.1 vector. The cloning procedures were performed by mean of total RNA extraction from the cells expressing high levels of the receptor. Subsequently a retro-transcription reaction was carried out according to the manufacturer's instructions. Specific oligonucleotide PCR primers external to the putative open reading frame (ORF) of the human receptor sequence were designed for PCR confirmation of stable transfection. PCR reactions to ascertain stable transfection were performed in $MgCL_2$ (1.5 mM), dNTP (1 mM), oligonucleotides (100 pmol), Taq Gold (0.5 U, PerkinElmer), with an annealing temperature of 55° C. The PCR product was ligated to an expression vector by utilizing the pCDNA3.1N5-His©TOPO®TA Expression kit (Invitrogen, Italy) according to the manufacturer's instructions. Cloned sequences were verified by sequencing.

1321N1 cell lines were stably transfected with GPCR22 cloned in pCDNA3.1 expression vectors (Invitrogen). 1321N1 cells were seeded at 150,000 cells/dish. Transfections were performed 24 hours after seeding with 2 ug DNA and 4 ul lipofectamine (Life Technologies). DNA Selection was performed using 600 ug/ml geneticin. After selection individual colonies were maintained in 300 ug/ml geneticin.

Example 4: GPCR22 Mediated Intracellular Effects

Figure 7A:
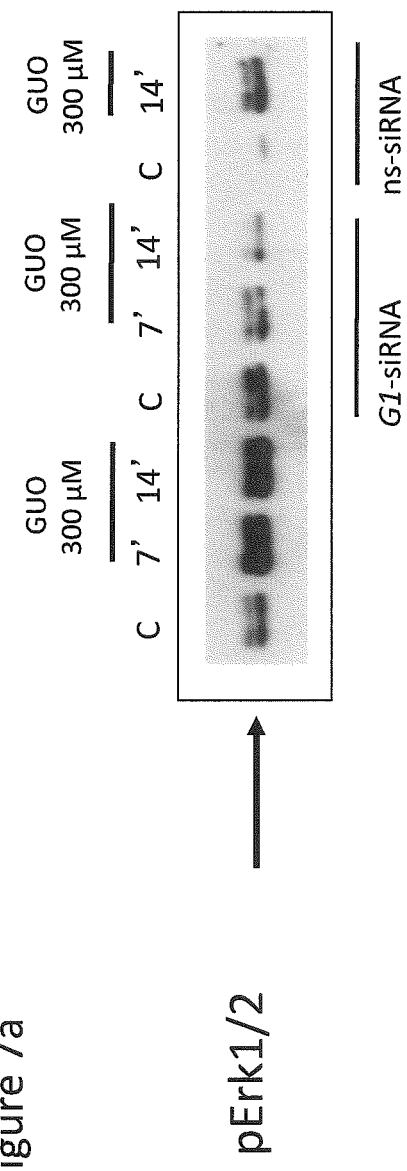
FIG. 7a is a photograph of a Western Blot showing Erk 1/2 phosphorylation by guanosine in cultured rat astrocytes and cultured rat astrocytes treated with siRNA for GPCR22 and ns-siRNA.
Figure 7B:
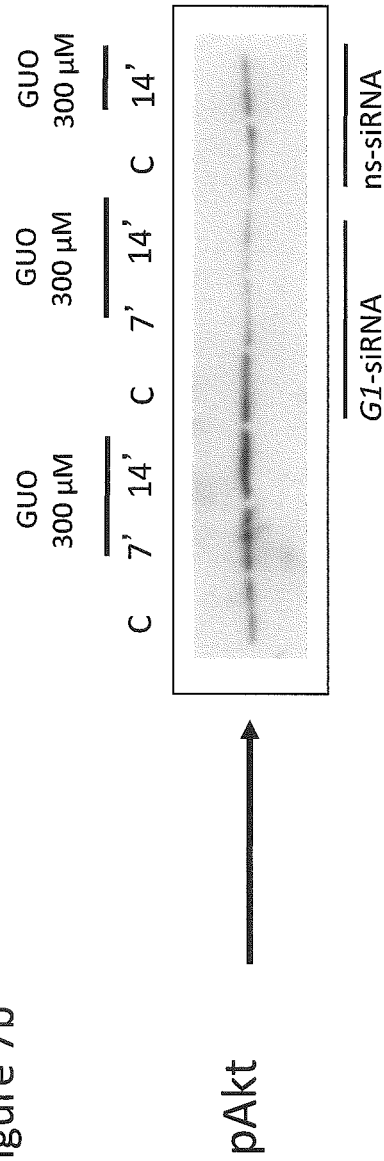
FIG. 7b is a photograph of a Western Blot showing Akt phosphorylation by guanosine in cultured rat astrocytes and cultured rat astrocytes treated with siRNA for GPCR22 and ns-siRNA.

Phosphorylation of Erk 1/2 and Akt:

FIGS. 7a and 7b, respectively, show that the phosphorylation of Erk 1/2 and Akt by guanosine (300 µM) is inhibited in cultured rat brain astrocytes treated with si-RNA for GPCR22; thus lending support that GPCR22 is indeed a G-Protein Coupled Receptor for guanosine, and analogues thereof. Similarly, as shown FIGS. 7c and 7d, respectively, in 1321N1 cells transfected with GPCR22 DNA (labelled "G1-pCMV Trans) so as to express the GPCR22 receptor, guanosine (300 µM) treatment of the cells resulted in phosphorylation of both Erk 1/2 and Akt compared to non-GPCR22-transfected 1321N1 cells (labelled "Non-Trans") which do not endogenously express GPCR22.

Figure 7E:
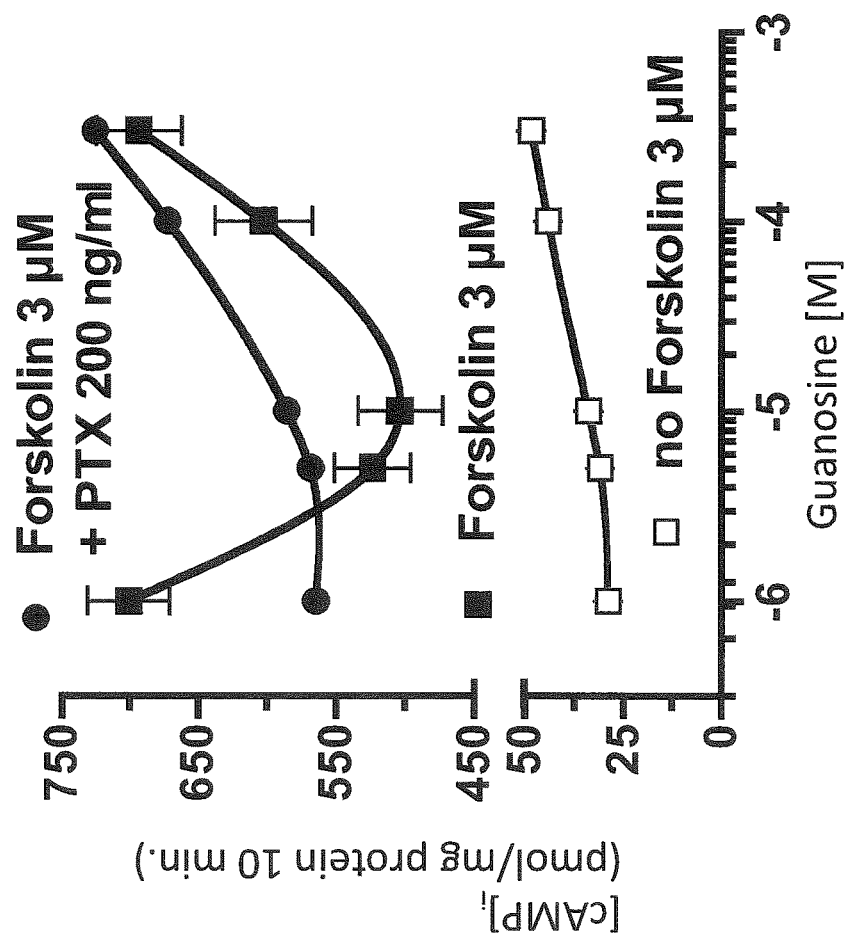
FIG. 7e is a graph showing the effect of guanosine on increasing intracellular cAMP concentrations in 1321N1 cells transfected with GPCR22 (G1) receptor DNA in the absence and in the presence of, 3 µM forskolin and 3 µM forskolin plus pertussis toxin (200 ng/ml, 16 h)

Intracellular cAMP Increase by Guanosine in 1321N1 Cells Transfected with GPCR22:

FIG. 7e shows the effects of increasing concentrations of exogenously applied guanosine on 1321N1 cell line transfected with GPCR22 (G1) receptor in the absence and in the presence of PTX (200 ng/ml, 16 h). Accordingly, it is shown that guanosine acts to produce cellular effects through GPCR22 and increase intracellular cAMP levels.

Example 5: Transfection of GPCR22 in *Drosophila* Schneider 2 (S2) Cells

A Full Length cDNA Clone of Rat GPCR22:

RNA from Rat striatum area was extracted using the Trizol method and then purified with Ambion RNA mini kit according to the manufacture instruction (Ambion RNA mini Kit, Cat: 12183020). cDNA of rGPCR22 was synthesized using Quanta Biosciences 95049-100 (qScript Flex cDNA synthesis kit), PCR polymerase (Invitrogen Platinum@ Taq DAN polymerase High Fidelity) and PCR water (GIBCO 10977 Ultrapure distilled water) following the manufacture's instructions. GPCR22 forward: CTC ATC TGC TGT TTC CAC GA (SEQ. ID NO: 5) and GPCR22 reverse CGG ATG TTA AGA GCC TGG AG (SEQ. ID NO: 6) were used. GPCR22 PCR product was tested by running 1% agarose gel following the instructions (Invitrogen). Gene Ruler 1 KB ladder was purchased from Thermo Scientific (SM3011). 5× loading buffer was used to load PCR product, and the gel was run at 100V until the front of the ladder reached the bottom of the gel. The results were detected under UV light. After confirmation of GPCR22 size with agarose gel, the correct band was cut and PCR product (cDNA of GPCR22 whole sequence) was extracted from the gel using Qiaex II Gel extraction kit (Qiagen 20021) as instructed by the manufacture. The extracted GPCR22 whole sequence was sent for sequencing to confirm the identity (Mobix service at McMaster University).

Preparation of GPCR22/pMTN5/HisA Plasmid DNA for Transfection:

The restriction enzyme sequences were added to the primers described as follows. Primers for GPCR22: Kpn I was added to the forward sequence and Apa I to the reverse sequence for whole cloned sequence of GPCR22. Extra base was also added for easier digestion. Restriction enzyme recognition sequence for the restriction enzymes used is underlined as follows—GPCR22 forward: Kpn I 5'-TAG GGTACC ATG TCA GAA TTG TCA AT-3' (SEQ ID NO: 12); GPCR22 reverse: Apa I 5'-CTA GGGCCC CTA GTC TGT GAC AAC CT-3' (SEQ ID NO: 13). pMT-V5-HisA, pMT-V5-His-Lacz and pCoHygro vectors were used. The inducible expression vector pMT-V5-HisA has a metallothionein (MT) promoter, and was induced by the addition of copper sulfate to the culture medium. It was stored in DH5α E. Coli. in a −80° C. freezer. Vector extraction was done using Qiagen Qia prep-SPIN minikit (Qiagen 27104) or Qiagen Hispeed Plasmid Max kit (Cat: 12662) according to the instructions from the manufacture. Using the following primer to clone PMT and COPIA sequences from the extracted vector DNA, and gel extracted PCR product were sent for sequencing to confirm the pMT vector (Mobix service at McMaster University). Primer for pMT and COPA: PMT forward: CAT CTC AGT GCA ACT AAA (SEQ ID NO: 14); Copia forward: TGT TGG AAT ATA CTA TTC AAC CTA CM (SEQ ID NO: 15).

The GPCR22 PCR products or the pMT vector plasmid DNA extraction was prepared through the sequential digestion, first using the restriction enzyme Apa I (Fermentas, Cat# ER1415). The digested products were then separated with electrophoresis and extracted with Qiaex II Gel extraction kit (Qiagen 20021). The extracted product was then subjected to a second digestion with the restriction enzyme Kpn I (Fermentas, Cat# ER0521), and then separated using gel electrophoresis and extracted with Qiaex II Gel extraction kit for further ligation. GPCR22 PCR product was digested at 37° C. for 2.5 hr, and the vectors were digested at 37° C. for 1.5 hr. Both of the reactions were deactivated at 60° C. for 20 min after the digestion.

Figure 3:
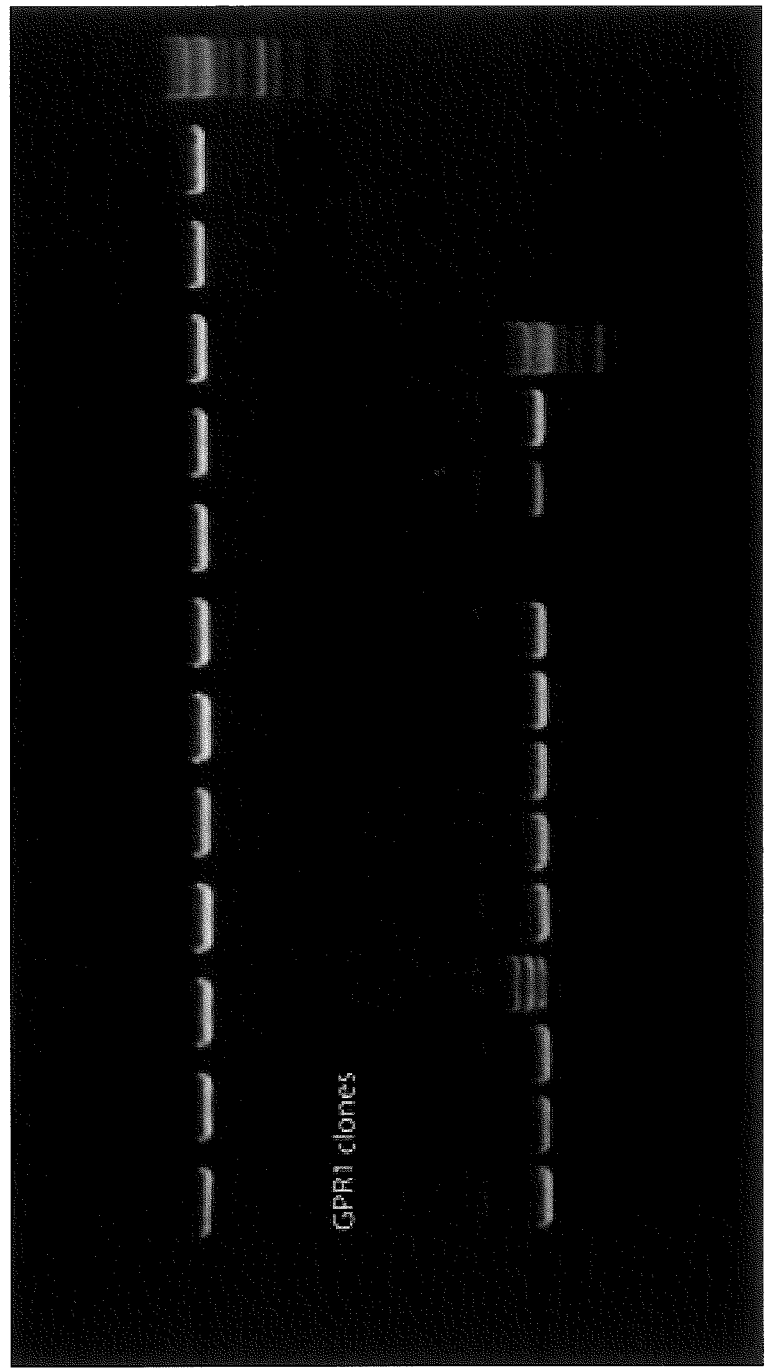
FIG. 3 is a photograph of a gel electrophoresis of Plasma DNA indicating positive cloning for GPCR22.

To calculate the amount of DNA required, 1:1 ratio (pMT/V5/HisA plasmid DNA:GPCR22 DNA), the amount was calculated according to the following formula: The amount of GPCR22 DNA=bp GPCR22 PCR product×the amount of Vector/bp of vector. Ligation was performed at 14° C. for overnight. Transformation of the ligated mix was done using one-short Top10 competitive E. Coli (Invitrogen, Cat#04040-03) following the manufacture's instruction. Clones were picked from LB plates and cultured separately at 250 rpm, 37° C., LB medium with 100 μg/ml Amp. Plasma DNA was extracted from clones and double digestion was performed with Apa I and Kpn I. After digestion, an electrophoretic gel was run to separate the DNA. The band size and number of bands was judged to foretell whether positive clones had been obtained, as shown in FIG. 3. The potential positive clones were sent for sequencing for confirmation. Once the positive E. Coli clones were confirmed, the culture was continued until a sufficient amount of GPCR22/pMTN5/HisA plasmid DNA for future transfection was obtained.

Transfection of Clone-Recombinant GPCR22 DNA to Drosophila Schneider 2 Cells (S2 Cells):

A calcium method was used for GPCR22 transfection into Drosophila Schneider 2 cells (S2) according to the manufacture's instruction (CalPhos Mammalian Transfection kit, Clontech, Cat No: 631312). Briefly, the Drosophila Schneider 2 cell line (also referred to herein as S2 cells) was purchased from Invitrogen (Cat: R690-07). Cells were cultured, passaged and stored according to the manufacture instruction. S2 cells were maintained at 25-28° C. in Schneider's Drosophila medium (GIBCO) supplemented with 10% heat-inactivated fetal calf serum, penicillin and streptomycin. 1.5×10$^6$ S2 cells per well were seeded with Drosophila Schneider 2 cell medium (S2 medium) and cultured for a day before transfection. Then, transfection was performed following the manufacture's recommended procedure. Following 24-hour culture, the S2 cells were collected into 1.5 ml eppendorf tube and labeled properly. The cells were then centrifuged at 3000 rpm for 2 min. in an eppendorf tube. The supernatant was re-suspended in 1 ml of S2 medium with 5 ml of 100 mM $CuSO_4$ solution (final concentration is 500 mM), then transferred one by one to new 12 well plate and incubated for 2 days.

Figure 4:
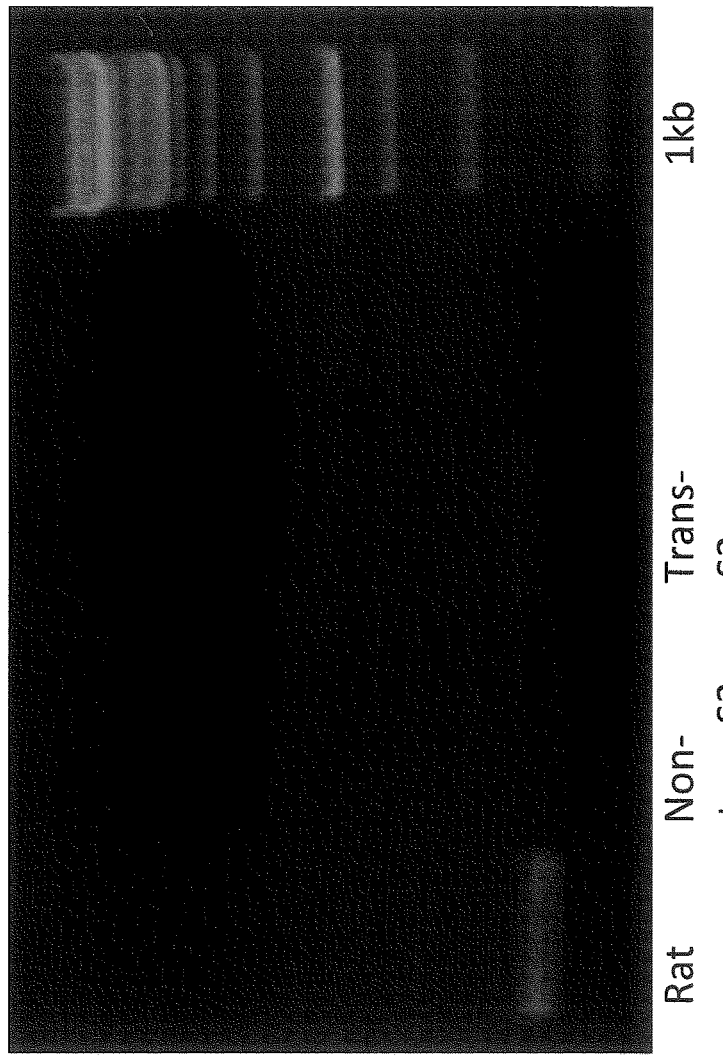
FIG. 4 is a photograph of a gel electrophoresis showing the expression of GPCR22 determined by real-time PCR from rat striatum, non-transfected normal Drosophila Schneider 2 cells and GPCR22 transfected Drosophila Schneider 2 cells.

Example 6: RT-PCR to Determine the Expression of GPCR22 from the Transfected S2 Cells For real-time PCR analysis total RNA was purified from S2 cells using Trizol (Invitrogen) according to the manufacturer's instructions and incubated with DNase. cDNA was prepared from 5 μg purified RNA using oligonucleotide dT primers. Real-time PCR was performed in an Eppendorf realplex2 PCR machine using SyBr green as a detection reagent. The following primers were used to detect the respective transcripts: Forward Primer (SEQ. ID NO: 5) for GPCR22, 2 μl; Reverse primer (SEQ. ID NO: 6) for GPCR22: 2 μl. Rat cDNA was used as positive control. FIG. 4 shows the PCR testing results that DNA for GPCR22 was successfully transfected into Drosophila Schneider 2 cells.

Example 7: Clone of Recombinated GPCR22 for Transfection

Sequences of Cloned GPCR22:

According to the agarose gel image of FIG. 4, the major band cloned (labeled "Trans-S2) from rat tissue is close to 1.5 KB. This band was cut and DNA was extracted for further sequencing confirmation. The sequencing results, using the forward primer of SEQ. ID NO: 5 and the reverse primer of SEQ. ID NO: 6, to obtain SEQ. ID NO: 1 and SEQ. ID NO: 2, showed that the GPCR22 (Trans-S2 band) cloned from rat stratum is 100% homology to rat GPCRC22 and 97% and 96% to mouse GPCR22 (SEQ. ID NO: 4).

Confirmation of Vector:

Sequence analysis (using Pubmed blast and align function) of vector showed that it is identical to the theoretical sequence for GPCR22.

Electrophoresis Identification of Positive Clone:

DNA was extracted from 8 E. Coli clones and double digested with Apa I and Kpn I. Both the undigested DNA and cut DNA samples were loaded for electrophoresis. Judging from the image electrophoresis image (FIG. 3), 6 out of 8 clones were positive for GPCR22. Samples from those positive DNA was sent for further sequencing confirmation.

Sequencing Confirmation of the Positive Clone:

The sequencing result showed that there were some "failed sequence reaction" identified as "N", as shown FIG. 8 at both ends of GPCR22-pMT-GPCR22-Forward. Therefore, the data in the middle (underlined sequence, 894 letters, in FIG. 8) was used to do further analysis (to blast in NCBI website) and the result are reported as following:

features in this part of subject sequence: component of oligomeric golgi complex 5; G protein-coupled receptor 22; Score=1596 bits (864), Expect=0.0; Identities=869/871 (99%), Gaps=2/871 (0%); Strand=Plus/Minus. Similarly, the sequencing result showed that there were some "failed sequence reaction" identified as "N", as shown FIG. 9 at both ends of GPCR22-pMT-GPCR22-Reverse. Therefore, the data in the middle (underlined sequence, 871 letters, in FIG. 9) was used to do further analysis. Features in this part of subject sequence: component of oligomeric golgi complex 5; G protein-coupled receptor 22; Score=1578 bits (854), Expect=0.0; Identities=865/871 (99%), Gaps=1/871 (0%); Strand=Plus/Minus.

Example 8: Confirmation of Successful Transfection of Cloned GPCR22 into S2 Cells Expression of GPCR22 from Transfected S2 Cells Determined by RT-PCR:

FIG. 4 (noted above), shows the expression of GPCR22 determined by real-time PCR from rat striatum (band labeled "Rat"), non-transfected normal S2 cells (band labeled "Non-transS2) and GPCR22 transfected S2 (band labeled "Trans-S2), from left to right, respectively, using Forward Primer/SEC). ID NO: 5) for GPCR22, and Reverse primer/SEQ. ID NO: 6) for GPCR22. This data indicates recombinated GPCR22 cDNA was successfully transfected into the S2 cells, while the non-transfected S2 cells did not express any detectable amount of GPCR22.

Example 9: Expression of GPCR22 Protein from Transfected S2 Cells Determined by Western Blotting Western Blotting and Protein Quantification:

S2 cells were harvested by centrifugation at 1000 g for 3 minutes and lysed on ice for 10 minutes in lysis buffer (Thermofisher with protease inhibiter added, M-PER® Mammalian Protein Extraction Reagent, Thermo Scientific cat#78503; Halt™ Protease and Phosphatase Inhibitor Cocktail, thermo cat#78440). Lysate was spun for 10 minutes at maximum speed, and the supernatant was added to sample loading buffer. Samples were separated by SDS-PAGE and analyzed by western blotting (Rathbone et al., 2011; Connell et al., 2013). Briefly, a rabbit polyclonal anti-GPCR22 antibody (NovateinBio, SH-A12465, MA, USA) was incubated over night at 1:1200 in 1.5% BSA in 1×TBST and a secondary anti-rabbit anti body 1:1000 in 1.5% BSA in 1×TBST was incubated for 1 hr 30 min. Bands were visualized using enhanced chemiluminescence (Amersham Biosciences, Piscataway, N.J.), and quantified on a Kodak Image Station 440CF (New Haven, Conn., USA). Antigens of interest were normalized to anti-GAPDH measured in the same sample.

Figure 10:
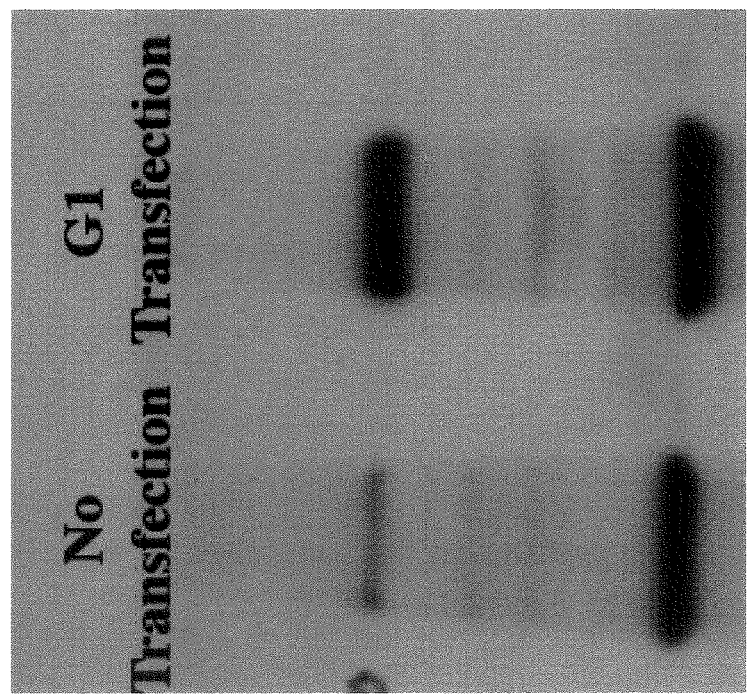
FIG. 10 is a photograph of a Western Blot showing GPCR22 (G1) protein expression in transfected Drosophila Schneider 2 cells.

Western blot technique and analysis using antibody against GPCR22 receptor showed GPCR22 protein expression in S2 cells following transfection indicating that the GPCR22 receptor DNA was successfully transfected into S2 cells and the encoded protein expressed. FIG. 10 shows the results of the Western blotting.

Example 10: Flow Cytometry Experiments

In order to determine whether guanosine produced any anti-apoptotic effects through a GPCR22-mediated mechanism, the effect of guanosine on apoptosis in GPCR22-transfected S2 cells was measured using flow cytometry techniques. Briefly, S2 cells were maintained in Schneider's *Drosophila* medium (GIBCO) supplemented with 10% heat-inactivated fetal calf serum, penicillin and streptomycin. For induction of apoptosis both receptor-transfected and non-transfected S2 cells were incubated in 1 μM actinomycin D (Sigma) for 6 hours at 25° C. Prior to the induction of apoptosis, to the S2 culture medium were either added 100 μM guanosine or the same amount of vehicle. After a 48 hr incubation with guanosine or vehicle, the cells were fixed with 4% PFA for fluorescent-immunostaining. The primary antibody Caspase-3 (10 μg/ml; R&D systems AF835) was incubated at room temperature for 1.5 hr and the secondary antibody (donkey anti rabbit Alexa488 (1:1800) was incubated at room temperature for 1 hr. After rinsing with PBS cells were re-suspend with "PBS+0.5% BSA" solution for flow cytometry reading using a 8 colour, 2 laser (488 nm, 633 nm, 405 nm) FACS (Canto) machine.

Figure 11B:
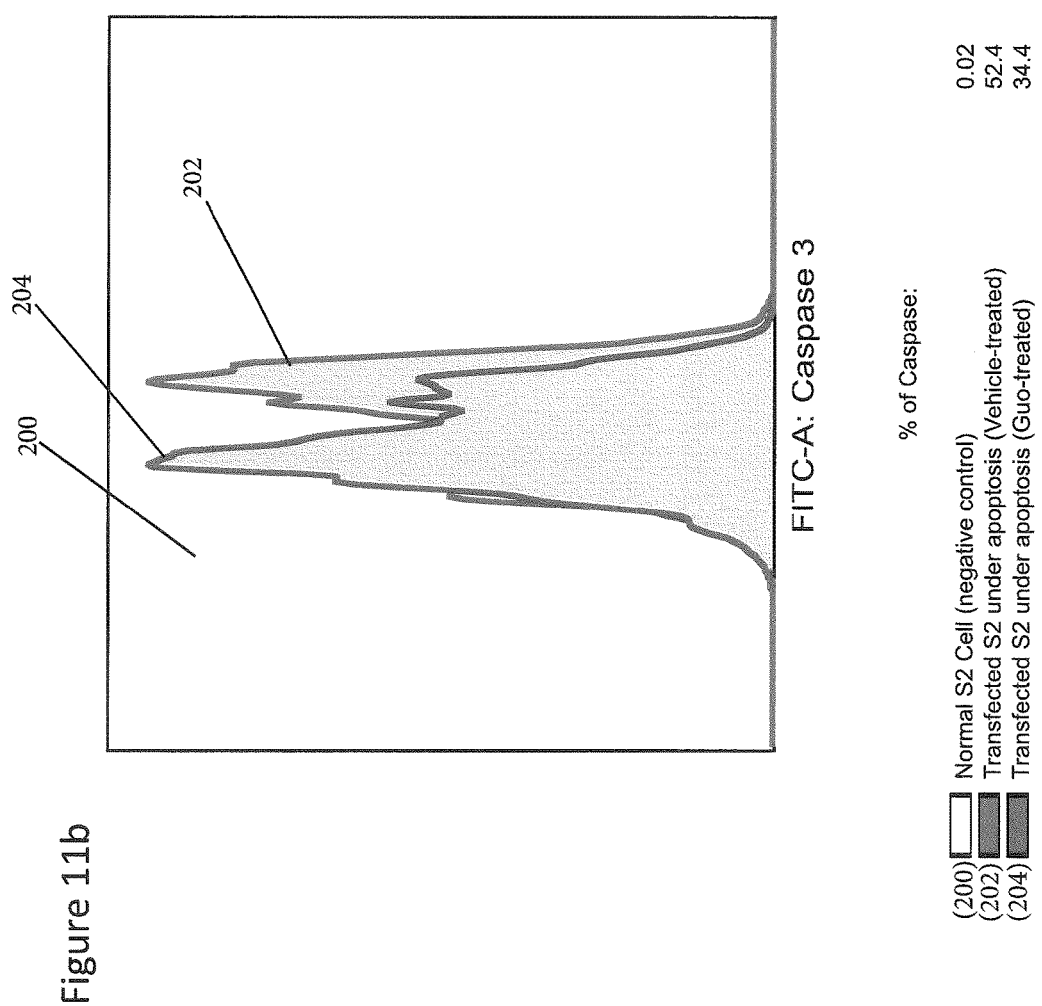
FIGS. 11 a to d are graphs of flow cytometry data showing the anti-apoptotic effects of guanosine on GPCR22 transformed *Drosophila* Schneider 2 cells in relation to Caspase-3 activity.
Figure 11C:
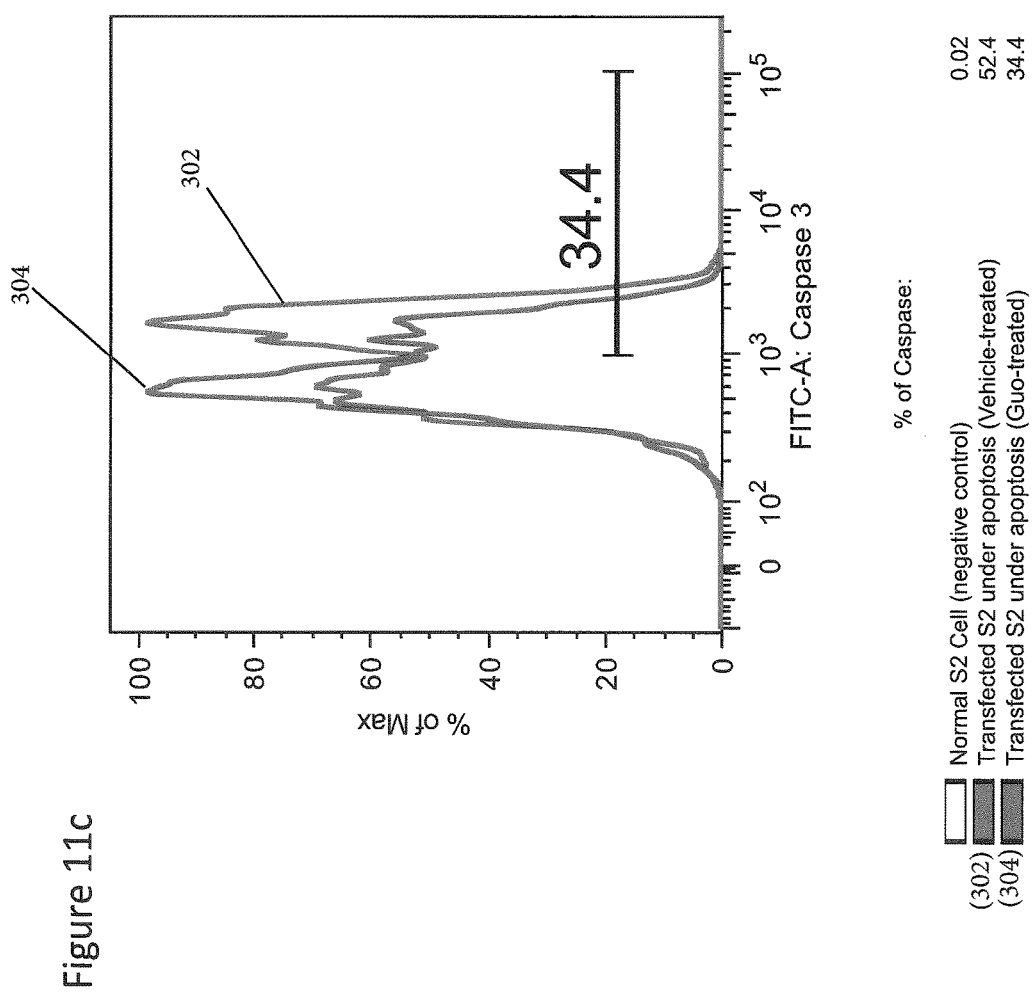
Figure 11D:
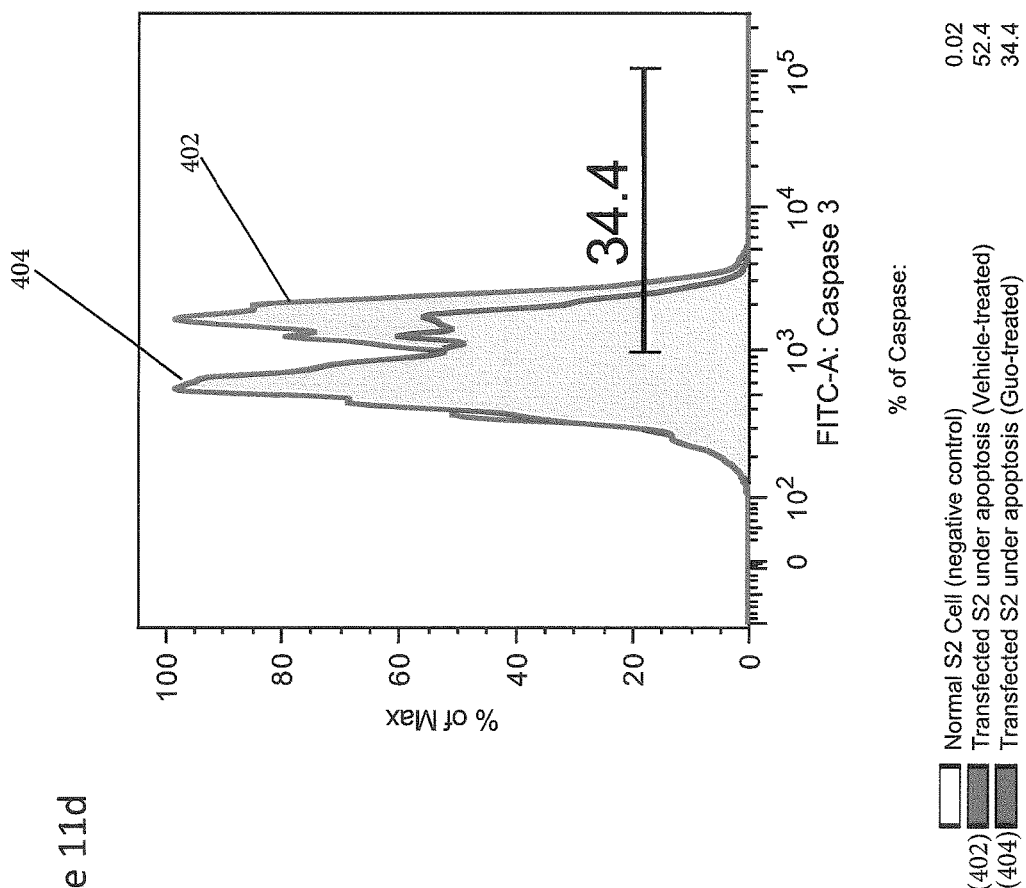

Effect of Guanosine Protecting Cells from Actinomycine-Induced Apoptosis is Regulated by GPCR22:

As shown in FIGS. 11 *a* to *d*, guanosine protected transfected S2 cells from apoptotic cell death when it was given to the cells before adding actinomycine into the medium, but had no effect on the normal non-transfected S2 cells, thus indicating that guanosine-induced anti-apoptosis is mediated by GPCR22 as indicated by Caspase-3 activation.

Example 11: $Ca^{2+}$ Determination and Quantification Experiments

Loading of Cells with Fluo-4:

Fluo-4 AM calcium imaging was used to visualize intracellular calcium concentration in the GPRC22-transfected and non-transfected S2 cells. A 2.5 mM stock solution of Fluo-4 Am dye (molecular Probes, Burlington, ON) was prepared in DMSO and 20% Pluronic F-127 and used to within a week. The S2 cell preparations were incubated with a final concentration of 5 μM fluo-4AM and 0.02% Pluronic F-127 in 1 ml S2 culture medium for 20 min at room temperature, then washed to allow for full de-esterification of AM esters. Imaging was carried out on an upright Nikon Eclipse FN-S2N upright fluorescence microscope using 10×/40× objectives with a filter to excite Fluo-4, a dye at 488 nm wavelength (peak excitation=494 nm and peak emission=516 nm) using a Lambda DG-4 illuminator (Sutter Instrument Co., Novato, Calif., USA). Images were captured using a Quantem 512SC camera with a frame rate of 5-10 frames per second and Nikon-NIS Elements, advanced research, imaging software.

Intracellular calcium concentration was created in the Nikon-NIS elements program using regions of interest (ROIs) per each experiment. ROIs were selected free hand and encompassed the cell body to be analyzed. The ROIs were tracked and the average pixel intensity was measured in that region for the duration of the recording. These measurements were then exported to Excel and Clampfit for further analysis of frequency and amplitude.

Figure 15:
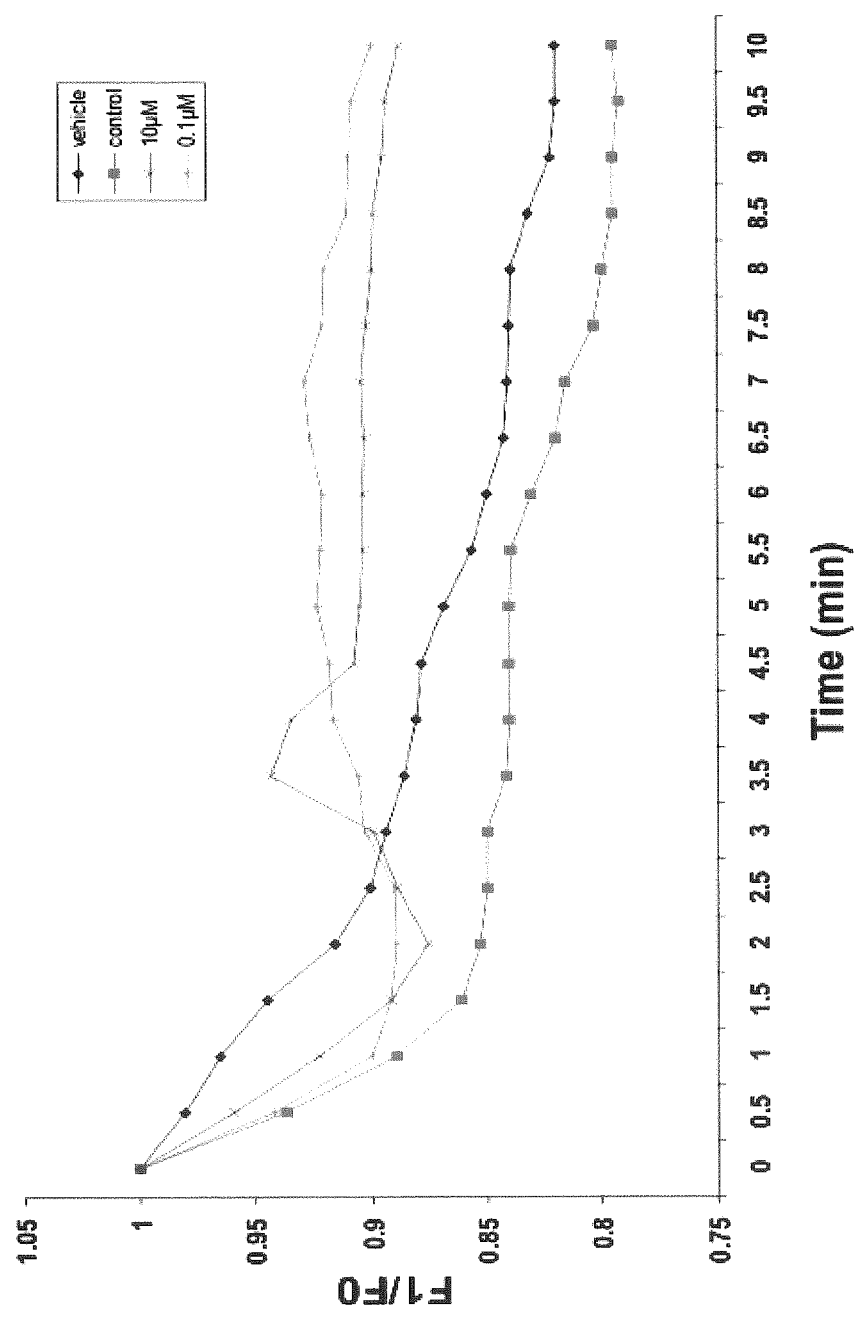
FIG. 15 is a graph showing GPCR22/guanosine mediated intracellular Ca2+ increase in GPCR22-transfected *Drosophila* Schneider 2 cells.

Intracellular calcium concentration of S2 cells was monitored at room temperature. 20-30 S2 cells were calculated to determine the average overall fluorescence signal intracellular calcium concentration. The fluorescence intensity was presented as the ratio F1/F0 in which the raw fluorescence intensity signals of a region of interest (ROI) was compared to the first fluorescence signal in that ROI throughout the recording. The Wilcoxon matched pairs t-test was used on two samples with equal variances to determine statistically significant differences at $P=0.05$. In each set of experiments, the exposure protocols for control and test conditions were identical. The results are shown in FIG. 15 where exogenously added guanosine is shown to elevate intracellular $Ca^{2+}$ levels.

Example 12: Guanosine-Induced Elevation of Intracellular $Ca^{2+}$ Levels is Mediated by GPCR22

Figure 12A:
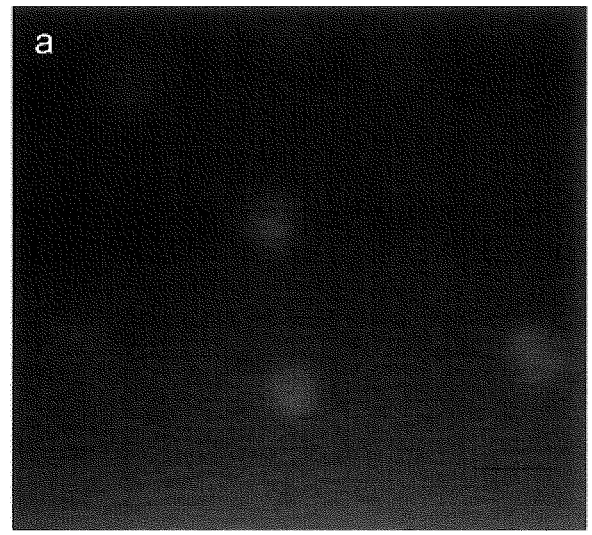
FIG. 12a is a fluorescence image showing the effect of guanosine on the level of intracellular $Ca^{2+}$ in non-GPCR22-transfected *Drosophila* Schneider 2 cells.
Figure 12B:
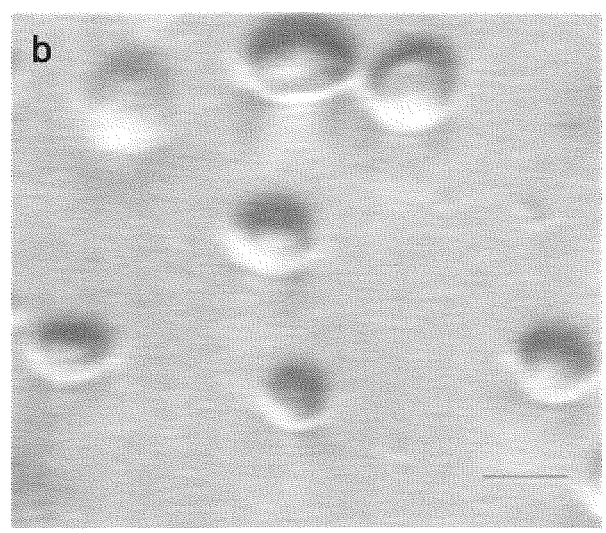
FIG. 12b is a fluorescence image showing the effect of guanosine on the level of intracellular $Ca^{2+}$ in GPCR22-transfected *Drosophila* Schneider 2 cells.
Figure 12C:
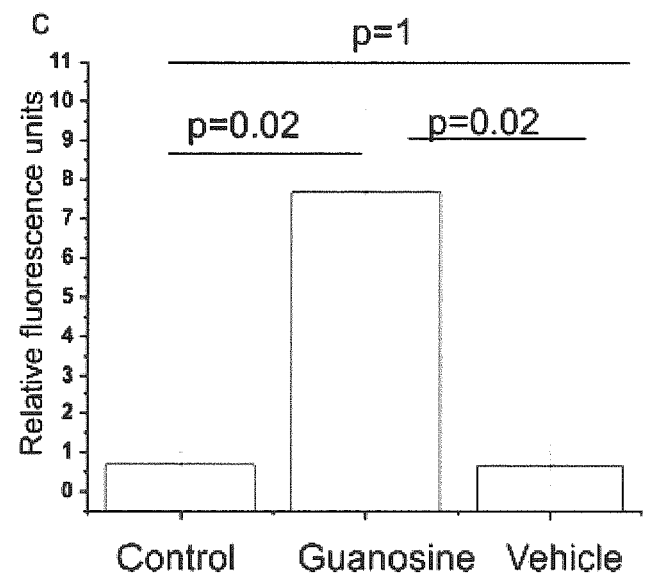
FIG. 12c is a graph showing the effect of guanosine on intracellular $Ca^{2+}$ concentration in GPCR22-transfected *Drosophila* Schneider 2 cells.
Figure 12D:
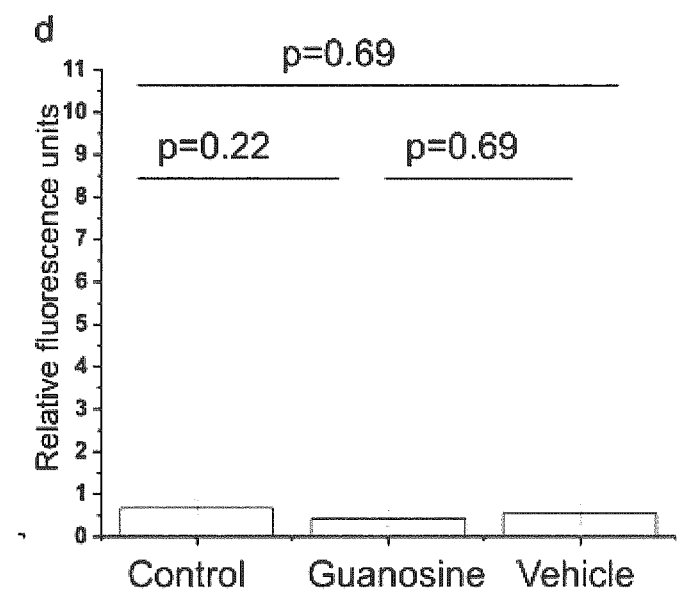
FIG. 12d is a graph showing the effect of guanosine on intracellular $Ca^{2+}$ concentration in non-GPCR22-transfected *Drosophila* Schneider 2 cells.

Effects of Guanosine Binding GPCR22 on the Intracellular Concentration of $Ca^{2+}$ ($[Ca^{2+}]i$):

FIG. 12a shows the effects of guanosine on intracellular $Ca^{2+}$ levels in normal, non-GPCR22 transfected cells, whereas FIG. 12b shows the effect of guanosine on intracellular $Ca^{2+}$ levels in S2 cells expressing GPCR22. Both FIG. 12a and FIG. 12b are fluorescence images showing intracellular $Ca^{2+}$ levels. It is clear from FIG. 12a and FIG. 12b that guanosine acts on GPCR22 to elevate intracellular $Ca^{2+}$ levels. FIG. 12c graphically shows guanosine-induced [Ca2+]i increase in transfected S2 cells expressing the GPCR22 receptor and FIG. 12d shows that guanosine does not induce a [Ca2-F]i increase in normal S2 cells. No significant difference of the intracellular calcium concentration on non-transfected S2 cells between vehicle treated and guanosine treated S2 cells were noted. Data are mean+/− SEM. *$P<0.05$, **$P<0.001$. Data are representative of at least 20 cells in each group. Scale bar=200 μm.

Figure 13E:
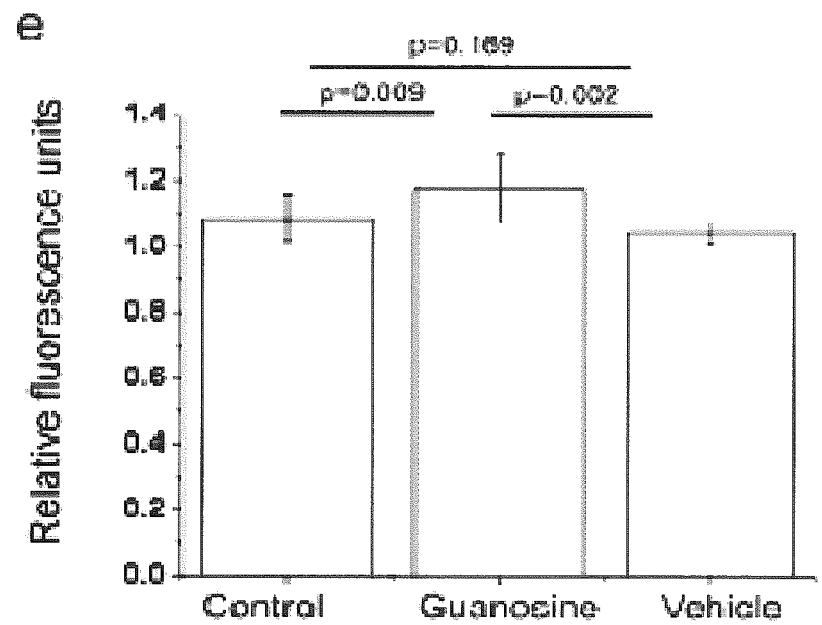
FIG. 13e is a graph showing an intracellular $Ca^{2+}$ response to guanosine in GPCR22-transfected *Drosophila* Schneider 2 cells.
Figure 13F:
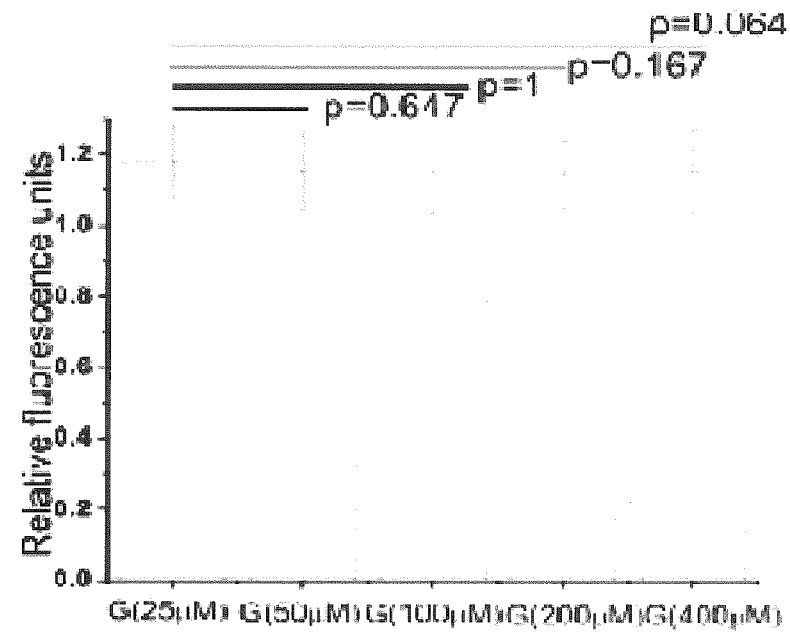
FIG. 13f is a graph showing high dose (25 μM-400 μM) guanosine-induced intracellular $Ca^{2+}$ response in GPCR22-transfected *Drosophila* Schneider 2 cells.
Figure 13G:
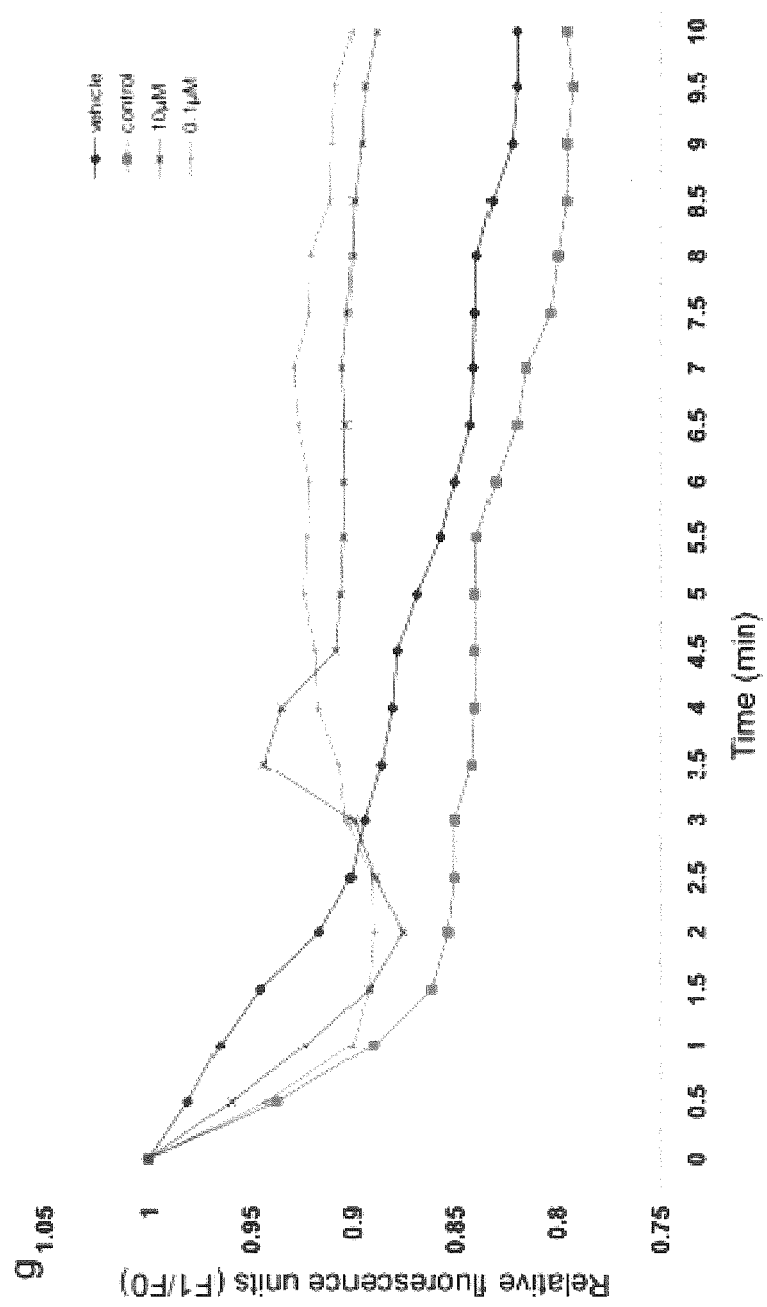
FIG. 13g is a graph showing a time course of low dose (0.1 μM-10 μM) guanosine-induced intracellular $Ca^{2+}$ response in GPCR22-transfected *Drosophila* Schneider 2 cells.

Effects of Guanosine Binding GPCR22 on the Intracellular Concentration of $Ca^{2+}$ ($[Ca^{2+}]i$) when Measured Immediately after Adding Guanosine:

FIGS. 13a to d show the sequence calcium imaging at time points 0 min, 0.5 min, 1 min and 2 min recording, respectively. Accordingly, a fast and transient fluorescence increase in intracellular $Ca^{2+}$ after guanosine (100 μM) addition to GPCR22-transfected S2 cells was observed. FIG. 13e shows a significant increase in intracellular $Ca^{2+}$ in GPCR22-transfected S2 cells following guanosine (25 μM) addition (at time point-1 min recording). FIG. 13f shows no significant difference after high dose guanosine (25 μM-400 μM) addition to GPCR22-transfected S2 cells, at time point-1 min recording. FIG. 13g shows a time course of low dose (0.1 μM to 10 μM) guanosine-induced [Ca2+]i increase in GPCR22-transfected 82 cells.

The data shows that guanosine significantly increases intracellular calcium level in GPCR22-transfected S2 cells in time (within 2 mins. after adding guanosine) and in a dose-depend manner (peak with 5 μM), while it had no effect on the calcium level of non-transfected S2 cells. This indicates that guanosine-dependent intracellular level of $Ca^{2+}$ elevation is dependent on and meditated by the GPCR22 receptor.

Example 13: GPCR22 Binding Using Radioactive Labeled Guanosine

The ability of GPCR22 receptor to bind to guanosine was assessed by performing competitive binding studies in the presence of cold guanosine. GPCR22 protein extracted from transfected 82 cells were used in performing receptor-binding studies. The binding of [$^3$H]-guanosine ("hot" guanosine) to GPCR22 receptor was performed in triplicate in a final volume of 125 μl assay buffer (pH 7.4, 50 mM Tris-HCl, 1 mM EDTA, 5 mM MgCl2, 0.1 mM DTT, 0.1 mM PMSF, 100 mg/ml bacitracin and 5 mg/ml soybean trypsin inhibitor) containing 10 nM [$^3$H]-guanosine and the following concentrations of unlabeled guanosine ("cold" guanosine) (0.01 μM, 0.1 μM, 1.0 μM, 10 μM, 100 μM and 1 mM) and 50 ug of protein. The incubation of the GPCR22 receptor protein with ligands was carried out at 25° C. for 75 min. At the end of the incubation period, the unbound ligands were separated by vacuum filtration through Whatman GF/B filters. The bound ligand-protein was further washed 3 times with 5 ml of Tris-EDTA buffer, pH 7.4 (50 mM Tris-HCl, 1 mM EDTA). The radioactive filters were placed in plastic counting vials containing 4 ml of scintillation fluid, equilibrated overnight in a dark environment and counted the next day in a Beckman LS5000 liquid scintillation counter Model 1780. Non-specific binding was also calculated by the addition of excess guanosine (10 mM).

Figure 14:
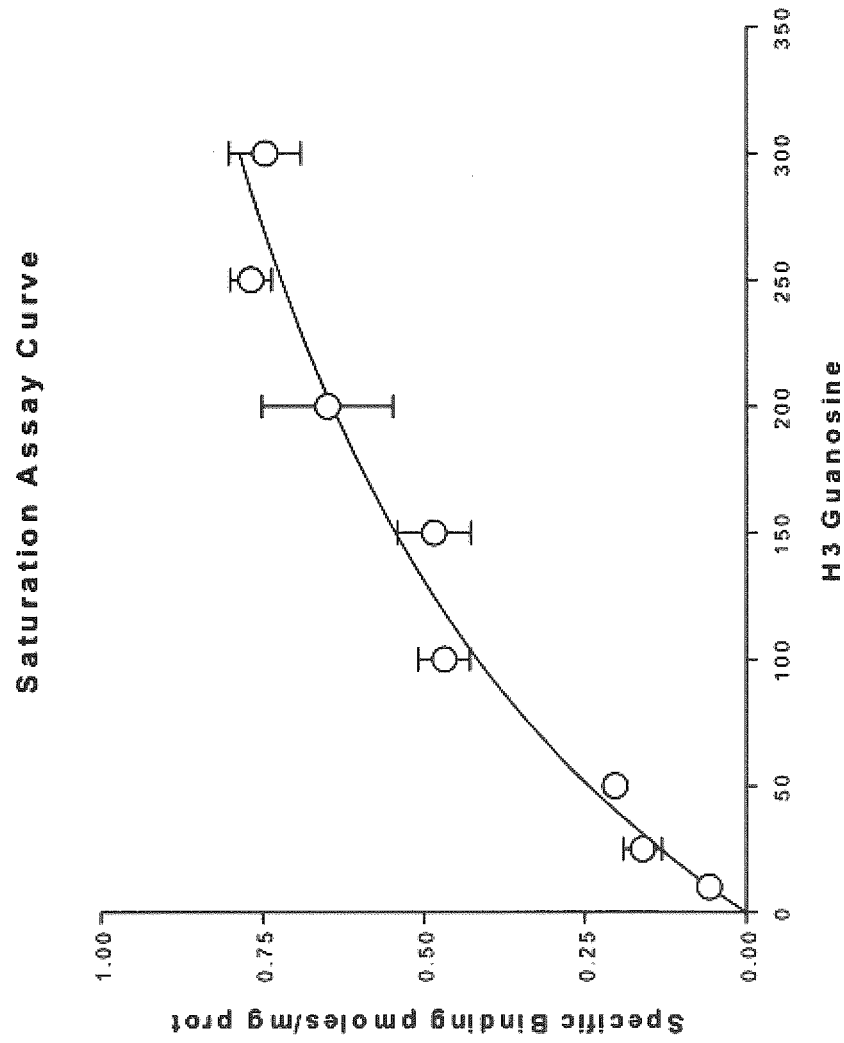
FIG. 14 is a Saturation Binding curve graph of guanosine to GPCR22 receptors.

[$^3$H]-Guanosine Binding Study:

The competition studies of the [$^3$H]-guanosine with unlabeled guanosine (cold) show that guanosine binds to GPCR22 in a single high affinity binding site with a KD of 170.9±39.79 nM and Bmax of 1.05±0.12 pmol mg$^{-1}$ protein as shown in FIG. 14. The FIG. 14 saturation curve analysis results are as follows:

Specific Binding Protein

Equation 1

Variables: BMAX=1.057; KD=170.9

Std. Error: BMAX=0.1207; KD=39.79

95% Confidence Intervals: BMAX=0.8038 to 1.311; KD=87.26 to 254.5

Goodness of Fit: Degrees of Freedom=18; $R^2$=0.9493; Absolute Sum of Squares=0.05014; Sy.x=0.05278

Data: Number of X values=8; Number of Y replicates=3; Total number of values=20; Number of missing values=4.

Accordingly, it has been shown that GPCR22 has a high-affinity binding site for guanosine.

Therefore, in light of above, it has been surprisingly discovered that the previously orphaned G-Protein Coupled Receptor 22 (GPCR22) is able to bind guanosine and is a cell-surface receptor therefor. Accordingly, cell-types devoid of this receptor may be transfected to express GPCR22 for use in screening of guanosine analogues and or ligand to the GPRC22 receptor for various medical, non-medical and research purposes. Additionally, transformed cells lines expressing GPCR22 may also be stably cultured for use in such experiments, among other uses. For example, in the embodiments disclosed herein, although not wishing to be limited thereto, 1321N1 human astrocytoma cells and *Drosophila* Schneider 2 cells may be transfected and made into transformed cell lines to express the GPCR22 receptor which is not otherwise endogenously expressed in the non-transfected counterparts of these cells. Other cell types may be readily apparent to one of skill in art from a reading of the techniques disclosed herein and may also be transfected to express GPCR22.

It is to be understood that the above description it is intended to be illustrative, and not restrictive. Many other embodiments will be apparent to those skilled in the art, upon reviewing the above description. The scope of the invention should, therefore, be determined with reference to the appended claims, along with the full scope of equivalents to which such claims are entitled.

Although the present invention has been described with reference to specific exemplary embodiments, it will be evident that various modifications and changes may be made to these embodiments without departing from the broader spirit and scope of the disclosed subject matter as defined by the appended claims.

What is claimed is:

1. A method for transforming a host cell to express a Guanosine-bindable G-Protein Coupled receptor, the method comprising:

transfecting a host cell with an expression vector, said expression vector comprising a polynucleotide sequence comprising SEQ. ID NO: 1 or SEQ. ID NO: 2, encoding for a polypeptide comprising an amino acid sequence comprising SEQ. ID NO: 3;

wherein said host cell, under the appropriate culture conditions, produces a polypeptide comprising said amino acid sequence of SEQ. ID NO: 3.

2. The method as defined in claim 1, wherein the polypeptide comprising SEQ. ID NO: 3 corresponds to GPCR22 and is expressed at the cell surface.

3. The method as defined in claim 2, wherein said host cell is a *Drosophila* Schneider 2 cell or a human astrocytoma 1321N1 cell.

4. A method for identifying a compound bindable to a G-Protein Coupled Receptor comprising:

contacting one or more candidate compounds with a host cell transformed to express a receptor comprising an amino acid sequence having at least 95% identity to SEQ. ID NO: 3, said amino acid sequence having at least 95% identity to SEQ. ID NO: 3 encoded by DNA comprising SEQ. ID NO: 1 or SEQ. ID NO: 2; and measuring an intracellular response associated with said one or more candidate compounds binding to said receptor.

5. The method as defined in claim 4, wherein said host cell is a *Drosophila* Schneider 2 cell or a human astrocytoma 1321N1 cell.

6. The method as defined in claim 4, wherein said one or more candidate compounds regulates apoptosis, intracellular calcium mobilization, intracellular protein phosphorylation or a second messenger intracellular pathway is an agonist, a partial agonist or an inverse agonist of the receptor.

7. The method as defined in claim 4, wherein said intracellular response is stimulation or inhibition of a cellular function associated with said receptor.

8. The method as defined in claim 7, wherein said stimulation or inhibition is indicative of a compound for regulating apoptosis, intracellular calcium mobilization, intracellular protein phosphorylation or a second messenger intracellular pathway.

9. A method for identifying a compound bindable to a G-Protein Coupled Receptor comprising: contacting one or more candidate compounds with a cell propagated from a host cell transformed to express a receptor comprising an amino acid sequence having at least 95% identity to SEQ. ID NO: 3, said amino acid sequence having at least 95% identity to SEQ. ID NO: 3 encoded by DNA comprising SEQ. ID NO: 1 or SEQ. ID NO: 2; and measuring an intracellular response associated with said one or more candidate compounds binding to said receptor.

10. The method as defined in claim 9, wherein said intracellular response is stimulation or inhibition of a cellular function associated with said receptor.

11. The method as defined in claim 9, wherein said stimulation or inhibition is indicative of a compound for regulating apoptosis, intracellular calcium mobilization, intracellular protein phosphorylation or a second messenger intracellular pathway.

12. The method as defined in claim 9, wherein said host cell is a *Drosophila* Schneider 2 cell or a human astrocytoma 1321N1 cell.

13. The method as defined in claim 9, wherein said one or more candidate compounds regulates apoptosis, intracellular calcium mobilization, intracellular protein phosphorylation or a second messenger intracellular pathway by way of being an agonist, a partial agonist or an inverse agonist of said receptor.

* * * * *

SEQUENCE LISTING

<160> NUMBER OF SEQ ID NOS: 17

<210> SEQ ID NO 1
<211> LENGTH: 1041
<212> TYPE: DNA
<213> ORGANISM: Rattus sp.
<220> FEATURE:
<221> NAME/KEY: modified_base
<222> LOCATION: (904)..(904)
<223> OTHER INFORMATION: a, c, t or g
<220> FEATURE:
<221> NAME/KEY: modified_base
<222> LOCATION: (923)..(923)
<223> OTHER INFORMATION: a, c, t or g
<220> FEATURE:
<221> NAME/KEY: modified_base
<222> LOCATION: (932)..(932)
<223> OTHER INFORMATION: a, c, t or g
<220> FEATURE:
<221> NAME/KEY: modified_base
<222> LOCATION: (982)..(982)
<223> OTHER INFORMATION: a, c, t or g
<220> FEATURE:
<221> NAME/KEY: modified_base
<222> LOCATION: (1001)..(1001)
<223> OTHER INFORMATION: a, c, t or g
<220> FEATURE:
<221> NAME/KEY: modified_base
<222> LOCATION: (1024)..(1024)
<223> OTHER INFORMATION: a, c, t or g
<220> FEATURE:
<221> NAME/KEY: modified_base
<222> LOCATION: (1032)..(1032)
<223> OTHER INFORMATION: a, c, t or g
<220> FEATURE:
<221> NAME/KEY: modified_base
<222> LOCATION: (1036)..(1036)
<223> OTHER INFORMATION: a, c, t or g

<400> SEQUENCE: 1

| | | | | | |
|---|---|---|---|---|---|
| tttctctctt | atttcactgt | cttcgtaggt | aaccttttg | tttcttttag | gatctatcca   60 |
| tgagttgtgt | attacagcgt | tattaggcat | gggatcagct | tcaactatgg | aaacaactcg  120 |
| cttttcatc | ttacttttta | agaccttttg | aaatttttgt | ctggtgaatg | catacaggag  180 |
| aggatggaat | atagttgttc | cataagccat | gactagaaaa | cacaatctta | attttactaa  240 |
| aaggtcactt | gggcctaaac | ataaaatggt | ggtatttaaa | acagaaattg | gtgtccaaca  300 |
| gagaagaaat | gtagaaataa | tcaataacga | cattttgaag | actcttttct | gcctctctcg  360 |
| tcgttcccgg | tgtcgtttca | cggctcgccg | gagggcaatt | attacagaaa | ctgaagttct  420 |
| cacaccaaat | acgacattcc | tcccaccact | gctttgcgac | atgtctgtgg | tctcatgtgt  480 |
| ggttagagag | attgtctttt | tcttccgggc | tttcttcttc | tggcctgttg | agaatctagt  540 |
| gcctatccgg | atattaagag | cctggagtat | cttggtgtat | gtgatcagca | tcacgataac  600 |
| tgtgaagaag | aagatgggga | tctgaactag | gaggtgatag | tacatcccga | gctcagtgta  660 |
| gtactcactt | gtgctgacac | acagcagtgt | cttgttttcc | cacgcatttc | cactttgaag  720 |
| gctgaaaaaa | ttgacttcaa | tgaagggaat | caggaatgag | aagaaagaaa | aaatccaaat  780 |
| ggacgtcatt | agcatcacag | ctctgcccat | tgtcagaatt | ctgtttgcag | gttttacaga  840 |
| gatgtcatat | ctgtccagag | taatagcaaa | aacgttgatt | gctgtggaaa | cacttgcaaa  900 |
| agancacaag | cttcgtggaa | acngcagatg | anagcagtgt | tcctctccag | tgagagcaga  960 |
| aggatcacta | tggttagagg | antacatccc | acacagatta | ntacatcaag | tacatggaga 1020 |
| ttcnttgtga | tnatgntact | g | | | 1041 |

<210> SEQ ID NO 2
<211> LENGTH: 892
<212> TYPE: DNA
<213> ORGANISM: Rattus sp.
<220> FEATURE:
<221> NAME/KEY: modified_base
<222> LOCATION: (5)..(5)
<223> OTHER INFORMATION: a, c, t or g
<220> FEATURE:
<221> NAME/KEY: modified_base
<222> LOCATION: (22)..(22)
<223> OTHER INFORMATION: a, c, t or g
<220> FEATURE:
<221> NAME/KEY: modified_base
<222> LOCATION: (32)..(32)
<223> OTHER INFORMATION: a, c, t or g
<220> FEATURE:
<221> NAME/KEY: modified_base
<222> LOCATION: (836)..(836)
<223> OTHER INFORMATION: a, c, t or g
<220> FEATURE:
<221> NAME/KEY: modified_base
<222> LOCATION: (840)..(840)
<223> OTHER INFORMATION: a, c, t or g
<220> FEATURE:
<221> NAME/KEY: modified_base
<222> LOCATION: (868)..(869)
<223> OTHER INFORMATION: a, c, t or g
<220> FEATURE:
<221> NAME/KEY: modified_base
<222> LOCATION: (880)..(880)
<223> OTHER INFORMATION: a, c, t or g

<400> SEQUENCE: 2
tatanatttg tggaaactac cntggtgagc cnaaaggccc ataaagcaac agcgaacagg      60
ggaaatacca actgctccaa aagaatgtgt ttttctcctg ttctggaaat caacatgcag     120
tctgaatcaa acgtcacggt gcagatgac attgaggaca tcgataccaa tatgtaccaa      180
ccactgtcat acccattaag ctttcaagtg tctctcactg gatttctcat gttagaaatt     240 gtgctgggc ttggtagcaa ccttaccgta ctggtacttt actgcatgaa atccaactta      300
atcagctctg tcagtaacat tatcacaatg aatctccatg tacttgatgt aataatctgt     360
gtgggatgta ttcctctaac catagtgatc cttctgctct cactggagag gaacactgct     420
ctcatctgct gtttccacga agcttgtgtt cttttgcaa gtgtttccac agcaatcaac      480 gttttttgcta ttactctgga cagatatgac atctctgtaa aacctgcaaa cagaattctg     540
acaatgggca gagctgtgat gctaatgacg tccatttgga ttttttcttt cttctcattc     600
ctgattccct tcattgaagt caatttttc agccttcaaa gtggaaatgc gtgggaaaac      660 aagcacactgc tgtgtgtcag cacaagtgag tactacactg agctcgggat gtactatcac    720
ctcctagttc agatccccat cttcttcttc acagttatcg tgatgctgat cacatacacc     780
aagatactcc aggctcttaa tatccggata ggcactagat tctcaacagg ccagangan      840 gcccggagaa aagacatctc tctaaccnna catgagaccn cagacatgtc gc           892

<210> SEQ ID NO 3
<211> LENGTH: 433
<212> TYPE: PRT
<213> ORGANISM: Homo sapiens

<400> SEQUENCE: 3

Met Cys Phe Ser Pro Ile Leu Glu Ile Asn Met Gln Ser Glu Ser Asn
1               5                   10                  15

Ile Thr Val Arg Asp Asp Ile Asp Asp Ile Asn Thr Asn Met Tyr Gln
            20                  25                  30

```
Pro Leu Ser Tyr Pro Leu Ser Phe Gln Val Ser Leu Thr Gly Phe Leu
             35                  40                  45
Met Leu Glu Ile Val Leu Gly Leu Gly Ser Asn Leu Thr Val Leu Val
 50                  55                  60
Leu Tyr Cys Met Lys Ser Asn Leu Ile Asn Ser Val Ser Asn Ile Ile
 65                  70                  75                  80
Thr Met Asn Leu His Val Leu Asp Val Ile Cys Val Gly Cys Ile
                 85                  90                  95
Pro Leu Thr Ile Val Ile Leu Leu Ser Leu Glu Ser Asn Thr Ala
                100                 105                 110
Leu Ile Cys Cys Phe His Glu Ala Cys Val Ser Phe Ala Ser Val Ser
            115                 120                 125
Thr Ala Ile Asn Val Phe Ala Ile Thr Leu Asp Arg Tyr Asp Ile Ser
130                 135                 140
Val Lys Pro Ala Asn Arg Ile Leu Thr Met Gly Arg Ala Val Met Leu
145                 150                 155                 160
Met Ile Ser Ile Trp Ile Phe Ser Phe Ser Phe Leu Ile Pro Phe
                165                 170                 175
Ile Glu Val Asn Phe Phe Ser Leu Gln Ser Gly Asn Thr Trp Glu Asn
                180                 185                 190
Lys Thr Leu Leu Cys Val Ser Thr Asn Glu Tyr Tyr Thr Glu Leu Gly
            195                 200                 205
Met Tyr Tyr His Leu Leu Val Gln Ile Pro Ile Phe Phe Thr Val
210                 215                 220
Val Val Met Leu Ile Thr Tyr Thr Lys Ile Leu Gln Ala Leu Asn Ile
225                 230                 235                 240
Arg Ile Gly Thr Arg Phe Ser Thr Gly Gln Lys Lys Ala Arg Lys
                245                 250                 255
Lys Lys Thr Ile Ser Leu Thr Thr Gln His Glu Ala Thr Asp Met Ser
            260                 265                 270
Gln Ser Ser Gly Gly Arg Asn Val Val Phe Gly Val Arg Thr Ser Val
        275                 280                 285
Ser Val Ile Ile Ala Leu Arg Arg Ala Val Lys Arg His Arg Glu Arg
290                 295                 300
Arg Glu Arg Gln Lys Arg Val Phe Arg Met Ser Leu Leu Ile Ile Ser
305                 310                 315                 320
Thr Phe Leu Leu Cys Trp Thr Pro Ile Ser Val Leu Asn Thr Thr Ile
                325                 330                 335
Leu Cys Leu Gly Pro Ser Asp Leu Leu Val Lys Leu Arg Leu Cys Phe
                340                 345                 350
Leu Val Met Ala Tyr Gly Thr Thr Ile Phe His Pro Leu Leu Tyr Ala
            355                 360                 365
Phe Thr Arg Gln Lys Phe Gln Lys Val Leu Lys Ser Lys Met Lys Lys
        370                 375                 380
Arg Val Val Ser Ile Val Glu Ala Asp Pro Leu Pro Asn Asn Ala Val
385                 390                 395                 400
Ile His Asn Ser Trp Ile Asp Pro Lys Arg Asn Lys Lys Ile Thr Phe
                405                 410                 415
Glu Asp Ser Glu Ile Arg Glu Lys Arg Leu Val Pro Gln Val Val Thr
            420                 425                 430

Asp

<210> SEQ ID NO 4
```

```
<211> LENGTH: 1410
<212> TYPE: DNA
<213> ORGANISM: Mus musculus

<400> SEQUENCE: 4
atgtcagaat tgtcaatgac atcatgtatc aatttgtgga aaactaccat ggtgagccca    60
aaggcccata aagcaacagt aaacaggcaa acaccaact gctccaaaag aatgtgtttt    120
tctcctgttc tggaaatcaa catgcagtct gaatcaaacg tcacggtgcg agatgacatt    180
gatgacatcg acaccaatat gtaccaacca ctgtcatacc cactaagctt tcaagtgtct    240
ctcactggat ttctcatgtt agagatcgtg ctggggcttg gcagcaacct taccgtcctg    300
gtactttact gcatgaaatc caacttaatc aactctgtca gtaacattat tacaatgaac    360
ctccatgtac ttgatgtcat aatttgtgtg ggatgcattc ctctaactat agtgatcctt    420
ctgctctcac tggagagtaa cactgctctc atctgctgtt ccacgaagc ttgtgtttcc    480
tttgcaagtg tttcgacagc aatcaacgtt tttgctatta ctctggacag atatgacatc    540
tctgtaaaac ctgcaaacag aattctgaca atgggcagag ctgtaatgct aatgacatcc    600
atttggattt tttctttctt ctcattcctg attcccttca ttgaagtaaa ttttttcagt    660
cttcaaagtg gaaatacatg ggcaaacaag acactgctgt gtgtcagtac aagtgaatac    720
tatactgagc tcgggatgta ctatcacctt ttggtgcaga tccccatctt cttcttcaca    780
gttatagtca tgttgatcac atacactaag atactccagg ctcttaacat ccgcataggc    840
actagattct caacaggaca gaagaagaaa gcccgaaaga aaaagacaat ctctctagct    900
acacatgaga ccacagacat gtcacaaagc agtggtggga ggaatgtcgt gtttggtgtg    960
agaacttcag tttctgtaat aattgccctc cggcgagccg tgaaacgcca ccgggaacga   1020
cgagaacggc agaaaagagt cttcaaaatg tcgttattga ttatttctac atttcttctc   1080
tgttggacac caatttctgt tttaaatacc accattctat gtttaggccc aagtgacctt   1140
ttagtaaaat taagattgtg tttttctagtc atggcttatg aacaacgat attccaccct   1200
ctcttgtatg cattcaccag acaaaagttt caaaaggtct aaagagtaa gatgaaaaag   1260
cgagttgttt ccatagttga agctgatccc atgcctaata acgctgtaat acacaactca   1320
tggatagatc ctaaaagaaa caaaaaggtt acctatgaag acagtgaaat aagagagaaa   1380
tgtttagtac ctcaggttgt cacagactag                                    1410

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctcatctgct gtttccacga                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggatgttaa gagcctggag                                                20
```

```
<210> SEQ ID NO 7
<211> LENGTH: 12
<212> TYPE: PRT
<213> ORGANISM: Unknown
<220> FEATURE:
<223> OTHER INFORMATION: Description of Unknown:
      Human, rat or mouse peptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(11)
<223> OTHER INFORMATION: Any amino acid

<400> SEQUENCE: 7

Xaa Xaa Xaa Cys Trp Xaa Pro Xaa Cys Xaa Xaa Asn
1               5                   10

<210> SEQ ID NO 8
<211> LENGTH: 12
<212> TYPE: PRT
<213> ORGANISM: Unknown
<220> FEATURE:
<223> OTHER INFORMATION: Description of Unknown:
      Human, mouse or rat peptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(11)
<223> OTHER INFORMATION: Any amino acid

<400> SEQUENCE: 8

Xaa Xaa Xaa Ser Trp Xaa Pro Xaa Ser Xaa Xaa Asn
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(2)
<223> OTHER INFORMATION: Any hydrophobic amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
```

```
<222> LOCATION: (4)..(4)
<223> OTHER INFORMATION: Cys or Ser
<220> FEATURE:
<221> NAME/KEY: MOD_RES
<222> LOCATION: (6)..(6)
<223> OTHER INFORMATION: Any hydrophobic amino acid
<220> FEATURE:
<221> NAME/KEY: MOD_RES
<222> LOCATION: (8)..(8)
<223> OTHER INFORMATION: Any hydrophobic amino acid
<220> FEATURE:
<221> NAME/KEY: MOD_RES
<222> LOCATION: (10)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Any hydrophobic amino acid
<220> FEATURE:
<221> NAME/KEY: MOD_RES
<222> LOCATION: (16)..(16)
<223> OTHER INFORMATION: Any amino acid

<400> SEQUENCE: 9

Xaa Xaa Xaa Xaa Trp Xaa Pro Xaa His Xaa Xaa Asn Xaa Xaa Thr Xaa
1               5                   10                  15

Phe

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(2)
<223> OTHER INFORMATION: Any hydrophobic amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Cys or Ser
<220> FEATURE:
<221> NAME/KEY: MOD_RES
<222> LOCATION: (6)..(6)
<223> OTHER INFORMATION: Any hydrophobic amino acid
<220> FEATURE:
<221> NAME/KEY: MOD_RES
<222> LOCATION: (8)..(8)
<223> OTHER INFORMATION: Any hydrophobic amino acid
<220> FEATURE:
<221> NAME/KEY: MOD_RES
<222> LOCATION: (9)..(9)
<223> OTHER INFORMATION: Cys or Ser
<220> FEATURE:
<221> NAME/KEY: MOD_RES
<222> LOCATION: (10)..(10)
<223> OTHER INFORMATION: Any hydrophobic amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
```

```
<221> NAME/KEY: MOD_RES
<222> LOCATION: (14)..(14)
<223> OTHER INFORMATION: Any hydrophobic amino acid
<220> FEATURE:
<221> NAME/KEY: MOD_RES
<222> LOCATION: (15)..(16)
<223> OTHER INFORMATION: Any amino acid

<400> SEQUENCE: 10

Xaa Xaa Xaa Xaa Trp Xaa Pro Xaa Xaa Xaa Xaa Asn Xaa Xaa Xaa Xaa
1               5                   10                  15

Phe

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(2)
<223> OTHER INFORMATION: Any hydrophobic amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Cys or Ser
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any hydrophobic amino acid
<220> FEATURE:
<221> NAME/KEY: MOD_RES
<222> LOCATION: (9)..(9)
<223> OTHER INFORMATION: Cys or Ser
<220> FEATURE:
<221> NAME/KEY: MOD_RES
<222> LOCATION: (10)..(10)
<223> OTHER INFORMATION: Any hydrophobic amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Any hydrophobic amino acid
<220> FEATURE:
<221> NAME/KEY: MOD_RES
<222> LOCATION: (15)..(16)
<223> OTHER INFORMATION: Any amino acid

<400> SEQUENCE: 11

Xaa Xaa Xaa Xaa Trp Xaa Pro Xaa Xaa Xaa Xaa Asn Xaa Xaa Xaa Xaa
1               5                   10                  15

Phe

<210> SEQ ID NO 12
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 12
tagggtacca tgtcagaatt gtcaat                                         26

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctagggcccc tagtctgtga caacct                                         26

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
catctcagtg caactaaa                                                  18

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgttggaata tactattcaa cctacaa                                        27

<210> SEQ ID NO 16
<211> LENGTH: 1208
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(6)
<223> OTHER INFORMATION: a, c, t or g
<220> FEATURE:
<221> NAME/KEY: modified_base
<222> LOCATION: (928)..(928)
<223> OTHER INFORMATION: a, c, t or g
<220> FEATURE:
<221> NAME/KEY: modified_base
<222> LOCATION: (931)..(931)
<223> OTHER INFORMATION: a, c, t or g
<220> FEATURE:
<221> NAME/KEY: modified_base
<222> LOCATION: (933)..(934)
<223> OTHER INFORMATION: a, c, t or g
<220> FEATURE:
<221> NAME/KEY: modified_base
<222> LOCATION: (950)..(951)
<223> OTHER INFORMATION: a, c, t or g
<220> FEATURE:
<221> NAME/KEY: modified_base
<222> LOCATION: (953)..(953)
```

```
<223> OTHER INFORMATION: a, c, t or g
<220> FEATURE:
<221> NAME/KEY: modified_base
<222> LOCATION: (963)..(963)
<223> OTHER INFORMATION: a, c, t or g
<220> FEATURE:
<221> NAME/KEY: modified_base
<222> LOCATION: (965)..(965)
<223> OTHER INFORMATION: a, c, t or g
<220> FEATURE:
<221> NAME/KEY: modified_base
<222> LOCATION: (968)..(968)
<223> OTHER INFORMATION: a, c, t or g
<220> FEATURE:
<221> NAME/KEY: modified_base
<222> LOCATION: (990)..(990)
<223> OTHER INFORMATION: a, c, t or g
<220> FEATURE:
<221> NAME/KEY: modified_base
<222> LOCATION: (992)..(993)
<223> OTHER INFORMATION: a, c, t or g
<220> FEATURE:
<221> NAME/KEY: modified_base
<222> LOCATION: (999)..(999)
<223> OTHER INFORMATION: a, c, t or g
<220> FEATURE:
<221> NAME/KEY: modified_base
<222> LOCATION: (1005)..(1005)
<223> OTHER INFORMATION: a, c, t or g
<220> FEATURE:
<221> NAME/KEY: modified_base
<222> LOCATION: (1013)..(1013)
<223> OTHER INFORMATION: a, c, t or g
<220> FEATURE:
<221> NAME/KEY: modified_base
<222> LOCATION: (1017)..(1017)
<223> OTHER INFORMATION: a, c, t or g
<220> FEATURE:
<221> NAME/KEY: modified_base
<222> LOCATION: (1021)..(1021)
<223> OTHER INFORMATION: a, c, t or g
<220> FEATURE:
<221> NAME/KEY: modified_base
<222> LOCATION: (1026)..(1027)
<223> OTHER INFORMATION: a, c, t or g
<220> FEATURE:
<221> NAME/KEY: modified_base
<222> LOCATION: (1030)..(1035)
<223> OTHER INFORMATION: a, c, t or g
<220> FEATURE:
<221> NAME/KEY: modified_base
<222> LOCATION: (1041)..(1042)
<223> OTHER INFORMATION: a, c, t or g
<220> FEATURE:
<221> NAME/KEY: modified_base
<222> LOCATION: (1045)..(1045)
<223> OTHER INFORMATION: a, c, t or g
<220> FEATURE:
<221> NAME/KEY: modified_base
<222> LOCATION: (1048)..(1051)
<223> OTHER INFORMATION: a, c, t or g
<220> FEATURE:
<221> NAME/KEY: modified_base
<222> LOCATION: (1054)..(1054)
<223> OTHER INFORMATION: a, c, t or g
<220> FEATURE:
<221> NAME/KEY: modified_base
<222> LOCATION: (1058)..(1058)
<223> OTHER INFORMATION: a, c, t or g
<220> FEATURE:
<221> NAME/KEY: modified_base
<222> LOCATION: (1067)..(1067)
<223> OTHER INFORMATION: a, c, t or g
<220> FEATURE:
<221> NAME/KEY: modified_base
<222> LOCATION: (1069)..(1070)
<223> OTHER INFORMATION: a, c, t or g
<220> FEATURE:
<221> NAME/KEY: modified_base
```

-continued

```
<222> LOCATION: (1072)..(1072)
<223> OTHER INFORMATION: a, c, t or g
<220> FEATURE:
<221> NAME/KEY: modified_base
<222> LOCATION: (1081)..(1081)
<223> OTHER INFORMATION: a, c, t or g
<220> FEATURE:
<221> NAME/KEY: modified_base
<222> LOCATION: (1083)..(1083)
<223> OTHER INFORMATION: a, c, t or g
<220> FEATURE:
<221> NAME/KEY: modified_base
<222> LOCATION: (1086)..(1090)
<223> OTHER INFORMATION: a, c, t or g
<220> FEATURE:
<221> NAME/KEY: modified_base
<222> LOCATION: (1092)..(1095)
<223> OTHER INFORMATION: a, c, t or g
<220> FEATURE:
<221> NAME/KEY: modified_base
<222> LOCATION: (1100)..(1101)
<223> OTHER INFORMATION: a, c, t or g
<220> FEATURE:
<221> NAME/KEY: modified_base
<222> LOCATION: (1103)..(1103)
<223> OTHER INFORMATION: a, c, t or g
<220> FEATURE:
<221> NAME/KEY: modified_base
<222> LOCATION: (1105)..(1106)
<223> OTHER INFORMATION: a, c, t or g
<220> FEATURE:
<221> NAME/KEY: modified_base
<222> LOCATION: (1109)..(1109)
<223> OTHER INFORMATION: a, c, t or g
<220> FEATURE:
<221> NAME/KEY: modified_base
<222> LOCATION: (1112)..(1116)
<223> OTHER INFORMATION: a, c, t or g
<220> FEATURE:
<221> NAME/KEY: modified_base
<222> LOCATION: (1118)..(1120)
<223> OTHER INFORMATION: a, c, t or g
<220> FEATURE:
<221> NAME/KEY: modified_base
<222> LOCATION: (1122)..(1123)
<223> OTHER INFORMATION: a, c, t or g
<220> FEATURE:
<221> NAME/KEY: modified_base
<222> LOCATION: (1125)..(1126)
<223> OTHER INFORMATION: a, c, t or g
<220> FEATURE:
<221> NAME/KEY: modified_base
<222> LOCATION: (1128)..(1130)
<223> OTHER INFORMATION: a, c, t or g
<220> FEATURE:
<221> NAME/KEY: modified_base
<222> LOCATION: (1133)..(1135)
<223> OTHER INFORMATION: a, c, t or g
<220> FEATURE:
<221> NAME/KEY: modified_base
<222> LOCATION: (1137)..(1140)
<223> OTHER INFORMATION: a, c, t or g
<220> FEATURE:
<221> NAME/KEY: modified_base
<222> LOCATION: (1142)..(1143)
<223> OTHER INFORMATION: a, c, t or g
<220> FEATURE:
<221> NAME/KEY: modified_base
<222> LOCATION: (1145)..(1157)
<223> OTHER INFORMATION: a, c, t or g
<220> FEATURE:
<221> NAME/KEY: modified_base
<222> LOCATION: (1159)..(1159)
<223> OTHER INFORMATION: a, c, t or g
<220> FEATURE:
<221> NAME/KEY: modified_base
<222> LOCATION: (1163)..(1164)
<223> OTHER INFORMATION: a, c, t or g
<220> FEATURE:
```

<221> NAME/KEY: modified_base
<222> LOCATION: (1168)..(1169)
<223> OTHER INFORMATION: a, c, t or g
<220> FEATURE:
<221> NAME/KEY: modified_base
<222> LOCATION: (1171)..(1171)
<223> OTHER INFORMATION: a, c, t or g
<220> FEATURE:
<221> NAME/KEY: modified_base
<222> LOCATION: (1174)..(1176)
<223> OTHER INFORMATION: a, c, t or g
<220> FEATURE:
<221> NAME/KEY: modified_base
<222> LOCATION: (1178)..(1180)
<223> OTHER INFORMATION: a, c, t or g
<220> FEATURE:
<221> NAME/KEY: modified_base
<222> LOCATION: (1184)..(1185)
<223> OTHER INFORMATION: a, c, t or g
<220> FEATURE:
<221> NAME/KEY: modified_base
<222> LOCATION: (1187)..(1187)
<223> OTHER INFORMATION: a, c, t or g
<220> FEATURE:
<221> NAME/KEY: modified_base
<222> LOCATION: (1189)..(1192)
<223> OTHER INFORMATION: a, c, t or g
<220> FEATURE:
<221> NAME/KEY: modified_base
<222> LOCATION: (1194)..(1200)
<223> OTHER INFORMATION: a, c, t or g
<220> FEATURE:
<221> NAME/KEY: modified_base
<222> LOCATION: (1202)..(1202)
<223> OTHER INFORMATION: a, c, t or g
<220> FEATURE:
<221> NAME/KEY: modified_base
<222> LOCATION: (1204)..(1208)
<223> OTHER INFORMATION: a, c, t or g

<400> SEQUENCE: 16

| | | | | | | |
|---|---|---|---|---|---|---|
| nnnnnnattt | gtggaaacww | cmmtggtgag | cmmaaaggcc | cataaagcaa | cagcgaacag | 60 |
| gggaaatacc | aactgctcca | aaagaatgtg | tttttctcct | gttctggaaa | tcaacatgca | 120 |
| gtctgaatca | aacgtcacgg | tgcgagatga | cattgaggac | atcgatacca | atatgtacca | 180 |
| accactgtca | tacccattaa | gctttcaagt | gtctctcact | ggatttctca | tgttagaaat | 240 |
| tgtgctgggg | cttggtagca | accttaccgt | actggtactt | tactgcatga | aatccaactt | 300 |
| aatcagctct | gtcagtaaca | ttatcacaat | gaatctccat | gtacttgatg | taataatctg | 360 |
| tgtgggatgt | attcctctaa | ccatagtgat | ccttctgctc | tcactggaga | ggaacactgc | 420 |
| tctcatctgc | tgtttccacg | aagcttgtgt | ttcttttgca | agtgtttcca | cagcaatcaa | 480 |
| cgttttttgct | attactctgg | acagatatga | catctctgta | aaacctgcaa | acagaattct | 540 |
| gacaatgggc | agagctgtga | tgctaatgac | gtccatttgg | atttttttctt | tcttctcatt | 600 |
| cctgattccc | ttcattgaag | tcaattttttt | cagccttcaa | agtggaaatg | cgtgggaaaa | 660 |
| caagacactg | ctgtgtgtca | gcacaagtga | gtactacact | gagctcggga | tgtactatca | 720 |
| cctcctagtt | cagatcccca | tcttcttctt | cacagttatc | gtgatgctga | tcacatacac | 780 |
| caagatactc | caggctctta | atatccggat | aggcactaga | ttctcaacag | gccagagaag | 840 |
| aaagcccgga | gaaaaagaca | atctctctaa | ccacacatga | gaccacagac | atgtcgcaaa | 900 |
| gcagtggtgg | gaggaatgtc | gtatttgngt | nannacttca | gtttctgtan | ntngccctcc | 960 |
| gcnanccntg | aaacgacacc | gggaacgacn | anngagcana | aagantctca | aangtcntta | 1020 |
| ntgatnnttn | nnnntttct | nnctntgnnn | ncanttcngt | ttaaatncnn | cntttatgtt | 1080 |
| ngnccnnnnn | annnngtaan | nananngggnt | cnnnnntnnn | gnntnngnnn | acnnntnnnn | 1140 | cnncnnnnnn nnnnnnnana aannaagnnt naannnannn aaannantnn nntnnnnnnn    1200 ancnnnnn    1208

<210> SEQ ID NO 17
<211> LENGTH: 1265
<212> TYPE: DNA
<213> ORGANISM: Artificial Sequence
<220> FEATURE:
<223> OTHER INFORMATION: Description of Artificial Sequence: Synthetic
      e
<220> FEATURE:
<221> NAME/KEY: modified_base
<222> LOCATION: (1)..(1)
<223> OTHER INFORMATION: a, c, t or g
<220> FEATURE:
<221> NAME/KEY: modified_base
<222> LOCATION: (3)..(3)
<223> OTHER INFORMATION: a, c, t or g
<220> FEATURE:
<221> NAME/KEY: modified_base
<222> LOCATION: (5)..(6)
<223> OTHER INFORMATION: a, c, t or g
<220> FEATURE:
<221> NAME/KEY: modified_base
<222> LOCATION: (9)..(24)
<223> OTHER INFORMATION: a, c, t or g
<220> FEATURE:
<221> NAME/KEY: modified_base
<222> LOCATION: (28)..(33)
<223> OTHER INFORMATION: a, c, t or g
<220> FEATURE:
<221> NAME/KEY: modified_base
<222> LOCATION: (35)..(35)
<223> OTHER INFORMATION: a, c, t or g
<220> FEATURE:
<221> NAME/KEY: modified_base
<222> LOCATION: (37)..(37)
<223> OTHER INFORMATION: a, c, t or g
<220> FEATURE:
<221> NAME/KEY: modified_base
<222> LOCATION: (39)..(39)
<223> OTHER INFORMATION: a, c, t or g
<220> FEATURE:
<221> NAME/KEY: modified_base
<222> LOCATION: (41)..(44)
<223> OTHER INFORMATION: a, c, t or g
<220> FEATURE:
<221> NAME/KEY: modified_base
<222> LOCATION: (46)..(54)
<223> OTHER INFORMATION: a, c, t or g
<220> FEATURE:
<221> NAME/KEY: modified_base
<222> LOCATION: (56)..(58)
<223> OTHER INFORMATION: a, c, t or g
<220> FEATURE:
<221> NAME/KEY: modified_base
<222> LOCATION: (60)..(66)
<223> OTHER INFORMATION: a, c, t or g
<220> FEATURE:
<221> NAME/KEY: modified_base
<222> LOCATION: (68)..(69)
<223> OTHER INFORMATION: a, c, t or g
<220> FEATURE:
<221> NAME/KEY: modified_base
<222> LOCATION: (72)..(73)
<223> OTHER INFORMATION: a, c, t or g
<220> FEATURE:
<221> NAME/KEY: modified_base
<222> LOCATION: (75)..(81)
<223> OTHER INFORMATION: a, c, t or g
<220> FEATURE:
<221> NAME/KEY: modified_base
<222> LOCATION: (83)..(104)
<223> OTHER INFORMATION: a, c, t or g
<220> FEATURE:
<221> NAME/KEY: modified_base -continued

```
<222> LOCATION: (108)..(108)
<223> OTHER INFORMATION: a, c, t or g
<220> FEATURE:
<221> NAME/KEY: modified_base
<222> LOCATION: (110)..(116)
<223> OTHER INFORMATION: a, c, t or g
<220> FEATURE:
<221> NAME/KEY: modified_base
<222> LOCATION: (118)..(122)
<223> OTHER INFORMATION: a, c, t or g
<220> FEATURE:
<221> NAME/KEY: modified_base
<222> LOCATION: (130)..(143)
<223> OTHER INFORMATION: a, c, t or g
<220> FEATURE:
<221> NAME/KEY: modified_base
<222> LOCATION: (149)..(149)
<223> OTHER INFORMATION: a, c, t or g
<220> FEATURE:
<221> NAME/KEY: modified_base
<222> LOCATION: (151)..(153)
<223> OTHER INFORMATION: a, c, t or g
<220> FEATURE:
<221> NAME/KEY: modified_base
<222> LOCATION: (156)..(158)
<223> OTHER INFORMATION: a, c, t or g
<220> FEATURE:
<221> NAME/KEY: modified_base
<222> LOCATION: (160)..(165)
<223> OTHER INFORMATION: a, c, t or g
<220> FEATURE:
<221> NAME/KEY: modified_base
<222> LOCATION: (170)..(170)
<223> OTHER INFORMATION: a, c, t or g
<220> FEATURE:
<221> NAME/KEY: modified_base
<222> LOCATION: (174)..(176)
<223> OTHER INFORMATION: a, c, t or g
<220> FEATURE:
<221> NAME/KEY: modified_base
<222> LOCATION: (178)..(180)
<223> OTHER INFORMATION: a, c, t or g
<220> FEATURE:
<221> NAME/KEY: modified_base
<222> LOCATION: (182)..(182)
<223> OTHER INFORMATION: a, c, t or g
<220> FEATURE:
<221> NAME/KEY: modified_base
<222> LOCATION: (185)..(185)
<223> OTHER INFORMATION: a, c, t or g
<220> FEATURE:
<221> NAME/KEY: modified_base
<222> LOCATION: (188)..(188)
<223> OTHER INFORMATION: a, c, t or g
<220> FEATURE:
<221> NAME/KEY: modified_base
<222> LOCATION: (190)..(190)
<223> OTHER INFORMATION: a, c, t or g
<220> FEATURE:
<221> NAME/KEY: modified_base
<222> LOCATION: (195)..(197)
<223> OTHER INFORMATION: a, c, t or g
<220> FEATURE:
<221> NAME/KEY: modified_base
<222> LOCATION: (202)..(202)
<223> OTHER INFORMATION: a, c, t or g
<220> FEATURE:
<221> NAME/KEY: modified_base
<222> LOCATION: (205)..(206)
<223> OTHER INFORMATION: a, c, t or g
<220> FEATURE:
<221> NAME/KEY: modified_base
<222> LOCATION: (208)..(208)
<223> OTHER INFORMATION: a, c, t or g
<220> FEATURE:
<221> NAME/KEY: modified_base
<222> LOCATION: (210)..(210)
<223> OTHER INFORMATION: a, c, t or g
<220> FEATURE:
```

```
-continued

<221> NAME/KEY: modified_base
<222> LOCATION: (217)..(217)
<223> OTHER INFORMATION: a, c, t or g
<220> FEATURE:
<221> NAME/KEY: modified_base
<222> LOCATION: (219)..(221)
<223> OTHER INFORMATION: a, c, t or g
<220> FEATURE:
<221> NAME/KEY: modified_base
<222> LOCATION: (232)..(235)
<223> OTHER INFORMATION: a, c, t or g
<220> FEATURE:
<221> NAME/KEY: modified_base
<222> LOCATION: (237)..(237)
<223> OTHER INFORMATION: a, c, t or g
<220> FEATURE:
<221> NAME/KEY: modified_base
<222> LOCATION: (239)..(240)
<223> OTHER INFORMATION: a, c, t or g
<220> FEATURE:
<221> NAME/KEY: modified_base
<222> LOCATION: (244)..(245)
<223> OTHER INFORMATION: a, c, t or g
<220> FEATURE:
<221> NAME/KEY: modified_base
<222> LOCATION: (250)..(250)
<223> OTHER INFORMATION: a, c, t or g
<220> FEATURE:
<221> NAME/KEY: modified_base
<222> LOCATION: (259)..(262)
<223> OTHER INFORMATION: a, c, t or g
<220> FEATURE:
<221> NAME/KEY: modified_base
<222> LOCATION: (266)..(269)
<223> OTHER INFORMATION: a, c, t or g
<220> FEATURE:
<221> NAME/KEY: modified_base
<222> LOCATION: (275)..(275)
<223> OTHER INFORMATION: a, c, t or g
<220> FEATURE:
<221> NAME/KEY: modified_base
<222> LOCATION: (277)..(277)
<223> OTHER INFORMATION: a, c, t or g
<220> FEATURE:
<221> NAME/KEY: modified_base
<222> LOCATION: (284)..(284)
<223> OTHER INFORMATION: a, c, t or g
<220> FEATURE:
<221> NAME/KEY: modified_base
<222> LOCATION: (294)..(295)
<223> OTHER INFORMATION: a, c, t or g
<220> FEATURE:
<221> NAME/KEY: modified_base
<222> LOCATION: (299)..(300)
<223> OTHER INFORMATION: a, c, t or g
<220> FEATURE:
<221> NAME/KEY: modified_base
<222> LOCATION: (321)..(322)
<223> OTHER INFORMATION: a, c, t or g
<220> FEATURE:
<221> NAME/KEY: modified_base
<222> LOCATION: (329)..(329)
<223> OTHER INFORMATION: a, c, t or g
<220> FEATURE:
<221> NAME/KEY: modified_base
<222> LOCATION: (332)..(332)
<223> OTHER INFORMATION: a, c, t or g
<220> FEATURE:
<221> NAME/KEY: modified_base
<222> LOCATION: (342)..(342)
<223> OTHER INFORMATION: a, c, t or g
<220> FEATURE:
<221> NAME/KEY: modified_base
<222> LOCATION: (344)..(345)
<223> OTHER INFORMATION: a, c, t or g
<220> FEATURE:
<221> NAME/KEY: modified_base
<222> LOCATION: (353)..(353)
<223> OTHER INFORMATION: a, c, t or g
```

```
<220> FEATURE:
<221> NAME/KEY: modified_base
<222> LOCATION: (361)..(361)
<223> OTHER INFORMATION: a, c, t or g
<220> FEATURE:
<221> NAME/KEY: modified_base
<222> LOCATION: (386)..(386)
<223> OTHER INFORMATION: a, c, t or g
<220> FEATURE:
<221> NAME/KEY: modified_base
<222> LOCATION: (518)..(518)
<223> OTHER INFORMATION: a, c, t or g
<220> FEATURE:
<221> NAME/KEY: modified_base
<222> LOCATION: (1263)..(1265)
<223> OTHER INFORMATION: a, c, t or g

<400> SEQUENCE: 17
nangnnccnn nnnnnnnnnn nnnnggannn nnntncnana nnnntnnnnn nnnnannnan      60
nnnnnntnna tnnannnnnn ntnnnnnnnn nnnnnnnnnn nnnncaangn nnnnnntnnn     120
nntagcttcn nnnnnnnnnn nnngatttnc nnnttnnnan nnnnnggggn tggnnngnnn     180
tncgnacngn acttnnngca tnaanncnan tatcagntnn ntcagtacat tnnnncnann     240
aatnncatgn acttgatgnn nnatcnnnnt gggangnatt cctntaacca tagnngatnn     300
tctgctctca ctggagagga nnactgctnt cntctgctgt tncnncgaag ctngtgtttc     360
nttttgcaag tgtttccaca gcaatnaacg ttttttgctat tactctggac agatatgaca    420
tctctgtaaa acctgcaaac agaattctga caatgggcag agctgtgatg ctaatgacgt     480
ccatttggat tttttctttc ttctcattcc tgattccntt cattgaagtc aattttttca     540
gccttcaaag tggaaatgcg tgggaaaaca agacactgct gtgtgtcagc acaagtgagt    600
actacactga gctcgggatg tactatcacc tcctagttca gatccccatc ttcttcttca     660
cagttatcgt gatgctgatc acatacacca agatactcca ggctcttaat atccggatag     720
gcactagatt ctcaacaggc cagaagaaga aagcccggaa gaaaaagaca atctctctaa     780
ccacacatga gaccacagac atgtcgcaaa gcagtggtgg gaggaatgtc gtatttggtg     840
tgagaacttc agtttctgta ataattgccc tccggcgagc cgtgaaacga caccgggaac    900
gacgagagag gcagaaaaga gtcttcaaaa tgtcgttatt gattatttct acatttcttc     960
tctgttggac accaatttct gttttaaata ccaccatttt atgtttaggc ccaagtgacc    1020
ttttagtaaa attaagattg tgttctctag tcatggctta tggagcaact atattccatc    1080
ctctcctgta tgcattcacc agacaaaaat ttcaaaaggt cttaaaaagt aagatgaaga    1140
agcgagttgt ttccatagtt gaagctgatc ccatgcctaa taacgctgta atacacaact    1200
catggataga tcctaaaaga aacaaaaagg ttacctacga agacagkkaa ataagagaga    1260
aannn                                                                1265
```